United States Patent
Desai et al.

(10) Patent No.: US 8,163,865 B2
(45) Date of Patent: Apr. 24, 2012

(54) BIOCOMPATIBLE AMINO ACID ANHYDRIDE POLYMERS

(75) Inventors: Shrojalkumar M. Desai, Little Canada, MN (US); Buddy D. Ratner, Seattle, WA (US)

(73) Assignee: University of Washington, Seattle, WA (US)

( * ) Notice: Subject to any disclaimer, the term of this patent is extended or adjusted under 35 U.S.C. 154(b) by 261 days.

(21) Appl. No.: 12/537,101

(22) Filed: Aug. 6, 2009

(65) Prior Publication Data

US 2010/0015205 A1 Jan. 21, 2010

Related U.S. Application Data

(63) Continuation of application No. PCT/US2008/053501, filed on Feb. 8, 2008.

(60) Provisional application No. 60/888,887, filed on Feb. 8, 2007.

(51) Int. Cl.
*C08G 69/08* (2006.01)

(52) U.S. Cl. ........... 528/310; 424/425; 528/61; 514/244

(58) Field of Classification Search ................... 424/425; 528/61, 310; 514/244
See application file for complete search history.

(56) References Cited

U.S. PATENT DOCUMENTS

| | | | |
|---|---|---|---|
| 3,830,792 A | 8/1974 | Tilak | |
| 4,351,337 A | 9/1982 | Sidman | |
| 4,891,225 A | 1/1990 | Langer | |
| 4,906,474 A | 3/1990 | Langer | |
| 5,326,632 A * | 7/1994 | Zenda et al. | 442/63 |
| 5,462,990 A | 10/1995 | Hubbell | |
| 6,642,363 B1 | 11/2003 | Mooney | |
| 2002/0151617 A1 | 10/2002 | Mao | |
| 2005/0013793 A1 | 1/2005 | Beckman | |
| 2006/0147409 A1 | 7/2006 | Pathak | |
| 2007/0275033 A9 * | 11/2007 | Moore et al. | 424/423 |

OTHER PUBLICATIONS

West, J.L., and J.A. Hubbell, "Polymeric Biomaterials with Degradation Sites for Proteases Involved in Cell Migration," Macromolecules 32(1):241-244, Jan. 1999.

* cited by examiner

*Primary Examiner* — Gregory Listvoyb
(74) *Attorney, Agent, or Firm* — Christensen O'Connor Johnson Kindness PLLC

(57) ABSTRACT

Biocompatible amino acid anhydride polymers for use in tissue engineering, and methods for their preparation and use.

23 Claims, 19 Drawing Sheets

BIOCOMPATIBLE AMINO ACID ANHYDRIDE POLYMERS

CROSS-REFERENCE TO RELATED APPLICATION

This application is a continuation of PCT/US2008/053501, filed Feb. 8, 2008, which claims the benefit of U.S. Provisional Application No. 60/888,887, filed Feb. 8, 2007. Each application is expressly incorporated herein by reference in its entirety.

BACKGROUND OF THE INVENTION

Biocompatible and biodegradable polymers have been prepared for use in many applications including drug delivery, artificial implants, tissue engineering, and organ regeneration. These polymers are generally designed for specific biomedical needs. Polymers used for drug delivery, for example, are generally unsuitable in objects intended for use in long-term implants, and polymers used for bone tissue regeneration are inappropriate for use in soft tissue engineering applications. Although there are many publications describing the use of rigid polymers for tissue engineering, soft or elastomeric polymers for use in soft-tissue scaffolds has been largely ignored.

Some biodegradable polymers are currently used for soft-tissue engineering applications. However, these materials suffer from several limitations, including the release of toxic acidic degradation products, mechanical incompliance with soft tissue, and catastrophic loss of mechanical strength.

The desire to use tissue-engineering methods to treat tragic diseases continues to grow. Esophageal cancer and its related disorders, for example, claims the lives of more than half a million people every year. In severe cases, a surgeon will remove a large portion of the esophagus and graft a section of the intestine in its place or connect it to an upper portion of the stomach. Leakage and malnutrition, or rejection, often occur.

Esophageal tissue engineering (ETE), based on the synthesis and use of degradable polymeric scaffolds, may help prevent or otherwise minimize these problems. Unlike many applications involving biocompatible materials, ETE requires the synthesis of scaffold materials with unique mechanical, morphological, and degradation properties.

A need exists for new biocompatible polymers suitable for use in ETE and other tissue engineering applications to address these complex issues and growing needs. The present invention fulfills this need and provides further related advantages.

SUMMARY OF THE INVENTION

The present invention relates to biocompatible amino acid anhydride polymers for use in tissue engineering, and methods for their preparation and use.

In one aspect, the invention provides a polymer obtainable by the process of reacting a diisocyanate prepolymer with a diamino acid anhydride to provide a polymer, where the diisocyanate prepolymer is prepared by covalently coupling a first diisocyanate compound to a second diisocyanate compound by reaction with a diol or hydroxy acid, and where the diamino acid anhydride is prepared by forming an anhydride from a first α-amino acid and a second α-amino acid.

In one embodiment, the invention provides a polymer that includes repeating units having the structure:

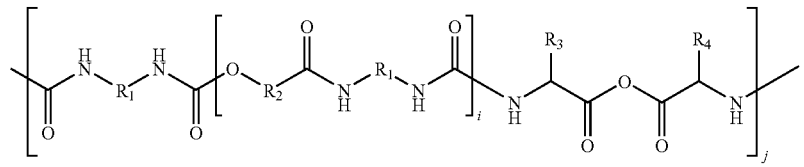

where $R_1$ includes $-(CH(COOCH_3)(CH_2)_4)-$ and $-(CH_2)_k-$, where k is an integer from 1 to 5;
$R_2$ is selected from $-(CH_2CH_2O)_n-$, $-(C(=O)(CH_2)_5O)_n-$, $-(C(=O)CH(CH_3)O)_n-$, $-(C(=O)CH_2O)_n-$, and $-(C(=O)CH(CH_3)O)_n-(C(=O)CH_2O)_m-$, where n is an integer from 1 to 1000 and m is an integer from 1 to 1000;
$R_3$ and $R_4$ are independently selected from α-amino acid side chains and their stereoisomers;
i is an integer from 1 to 1000; and
j is an integer from 1 to 1000.

In one embodiment, the invention provides a polymer that includes repeating units having the structure:

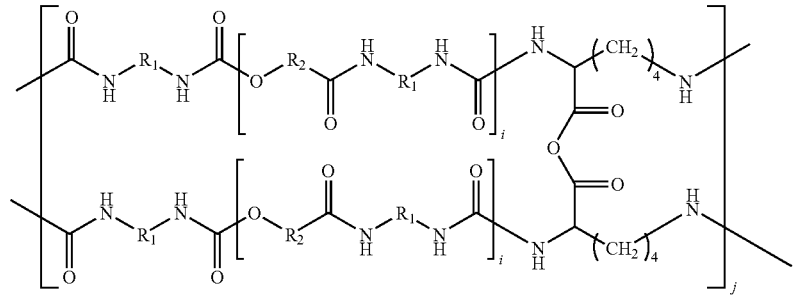

where $R_1$ includes $-(CH(COOCH_3)(CH_2)_4)-$ and $-(CH_2)_k-$, where k is an integer from 1 to 5;
$R_2$ is selected from $-(CH_2CH_2O)_n-$, $-(C(=O)(CH_2)_5O)_n-$, $-(C(=O)CH(CH_3)O)_n-$, $-(C(=O)CH_2O)_n-$, and $-(C(=O)CH(CH_3)O)_n-(C(=O)CH_2O)_m-$, where n is an integer from 1 to 1000 and m is an integer from 1 to 1000;

i is an integer from 1 to 1000; and j is an integer from 1 to 1000.

In one aspect, the invention provides a biodegradable scaffold for soft tissue engineering including a polymer of the invention.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 2A and 2B schematically illustrate portions of two representative polymers of the invention;

FIG. 7 illustrates a portion of a representative polymer of the invention;

DETAILED DESCRIPTION OF THE INVENTION

The present invention relates to biocompatible amino acid anhydride polymers for use in tissue engineering, and methods for their preparation and use.

In one aspect, the invention provides a polymer obtainable by the process of reacting a diisocyanate prepolymer with a diamino acid anhydride to provide a polymer, where the diisocyanate prepolymer is prepared by covalently coupling a first diisocyanate compound to a second diisocyanate compound by reaction with a diol or hydroxy acid, and where the diamino acid anhydride is prepared by forming an anhydride from a first α-amino acid and a second α-amino acid.

Polymers of the invention are synthesized from diamino acid anhydride (DAAA) compounds that act as chain extenders in polyurea polymers. The DAAAs can be made using any of the naturally occurring amino acids (e.g., α-amino acids) and their stereoisomers, and any synthetic amino acid (non-natural). Polymers of the invention are linear or crosslinked (branched) depending on the R groups of the amino acids used. As used herein, the terms "R group" and "side chain" when made in reference to amino acids, are synonymous and refer to the amino acid side chain originating on the α-carbon of the α-amino acid. The R groups of the naturally occurring amino acids are well known to those of skill in the art, as is the nomenclature for naming the amino acids. DAAAs of the invention are formed by coupling the carboxylic acid groups of two amino acids. The amino acids used to make DAAAs useful in forming polymers of the invention may be the same or different. The preparation of a representative DAAA useful in the invention, dilysine anhydride, is described in Example 1.

In one embodiment, the first amino acid and the second amino acid are the same.

In one embodiment, the first amino acid and the second amino acid are different.

In one embodiment, the first amino acid and the second amino acid are independently selected from the group consisting of alanine, valine, leucine, isoleucine, proline, methionine, phenylalanine, tryptophan, glycine, serine, threonine, cysteine, tyrosine, asparagines, glutamine, aspartic acid, glutamic acid, lysine, arginine, and histidine.

In one embodiment, the first amino acid and the second amino acid are independently selected from the group consisting of lysine, serine, threonine, and tyrosine.

In one embodiment, the first amino acid is selected from the group consisting of alanine, valine, leucine, isoleucine, proline, methionine, phenylalanine, tryptophan, glycine, cysteine, asparagines, glutamine, aspartic acid, glutamic acid, arginine, and histidine.

In one embodiment, the second amino acid is selected from the group consisting of lysine, serine, threonine, and tyrosine.

In one embodiment, the first and second amino acids are lysine.

Figure 1:
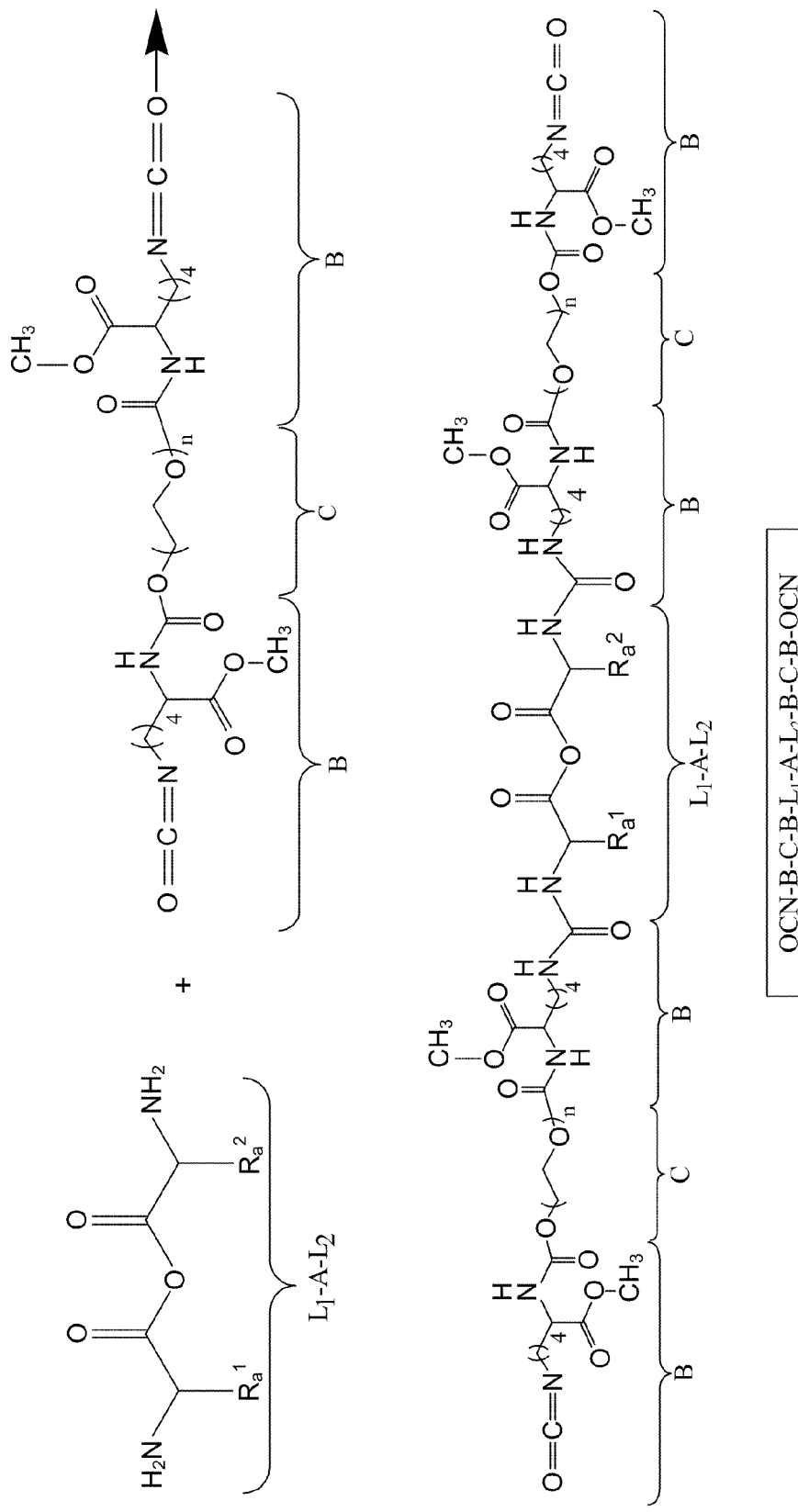
FIG. 1 schematically illustrates the synthesis of a compound useful in forming polymers of the invention.

The preparation of a representative polymer of the invention is illustrated schematically in FIG. 1. Referring to FIG. 1, the DAAA ($L_1$-A-$L_2$, a diamine formed by two amino acids linked through their carboxyl groups to form an anhydride, where $L_1$ and $L_2$ represent the first and second amino acids and A represents the anhydride, $L_1$ and $L_2$ can be the same or different) is used as a chain extender and is covalently coupled to two diisocyanate compounds (prepolymers, B—C—B, where B is a lysine isocyanate and C is a poly (ethylene oxide)) to provide a diisocyanate intermediate (OCN—B—C—B-$L_1$-A-$L_2$-B—C—B—NCO). Each of the DAAA amino groups reacts with a diisocyanate isocyanate group to form a urea linkage.

Prepolymers useful in the invention are formed by reacting at least two equivalents of diisocyanate (B) with a diol and/or hydroxy acid (C) to provide a diisocyanate having the structure (OCN—B—C—B—OCN) in the simplest form. The urethane chemistry used to form the prepolymers is known to those of skill in the art and there are many possible embodiments of the prepolymer. By further reacting the simple prepolymer described above with (the same or other) diols or hydroxy acids and isocyanates, any number of prepolymers can be formed, so long as the prepolymer has isocyanate functionality for coupling to the amines of the DAAA, for example, OCN—B—C—B—C—B—C—B—NCO. The diisocyanates, hydroxy acids, and diols need not all be the same, and the properties of the polymers of the invention can be varied based on the size and composition of the prepolymer segments.

Representative diols useful in the invention include poly(ethylene glycol) (PEG). Representative hydroxy acids useful in the invention include 6-hydroxyhexanoic acid, polycaprolactone (PCL), lactic acid, poly(lactic acid) (PLA), glycolic acid, poly(glycolic acid) (PGA), and PLA-PGA copolymers (PLGA). Polymeric diols and hydroxy acids useful in making the polymers of the invention have from 1 to 1000 repeating units. Polymers of the invention incorporating polymeric diols and polymeric hydroxy acids can be elastomers.

The polymers of the invention can include one or more segments made from different diols or hydroxy acids (i.e., the polymers of the invention can be made from one or more different prepolymers, each derived from a different diol or hydroxy acid).

Representative diisocyanates useful in the invention include lysine diisocyanate and $C_1$-$C_5$ alkyl diisocyanates (e.g., butane ($C_4$) diisocyanate).

In one embodiment, the first diisocyanate and the second diisocyanate are the same.

In one embodiment, the first diisocyanate and the second diisocyanate are different.

In one embodiment, the first and second diisocyanate compounds are lysine diisocyanate.

Because the targeted uses of the invention are biological, particularly useful prepolymers are biocompatible and their degradation products are biotolerable. As used herein, the term "biocompatible" refers to the ability to perform as a substrate that will support the appropriate cellular activity, including the facilitation of molecular and mechanical signaling systems, in order to optimize tissue regeneration, without eliciting any undesirable effects in those cells, or inducing any undesirable local or systemic responses in the eventual host. As used herein, the term "biotolerable" refers to the degradation products of the polymer of the invention and their ability to be tolerated in vivo without significant side effects.

If the R group of an amino acid used to form a DAAA ($R_a^1$ or $R_a^2$ in FIG. 1) includes a group capable of reacting with an isocyanate to form a covalent bond (e.g., an amino, hydroxyl, or phenol) then the resulting polymer can be crosslinked due to the reactive R group providing a site for crosslinking between polymer chains. Representative natural amino acids that contain reactive R groups include lysine (—$(CH_2)_4NH_2$), serine (—$CH_2OH$), threonine (—$CH(CH_3)OH$), and tyrosine (—$CH_2C_6H_4OH$). If a reactive group is not present in the R group (all sixteen other natural amino acids) then the resulting polymer will be linear. FIGS. 2A and 2B illustrate two examples of representative linear polymers of the invention, with the repeat unit in brackets. The difference between the polymers of FIGS. 2A and 2B is the difference in the prepolymer (i.e., B—C—B and B—C—B—C—B—C—B). The synthesis of a representative linear polymer of the invention is described in Example 2.

Figure 3:
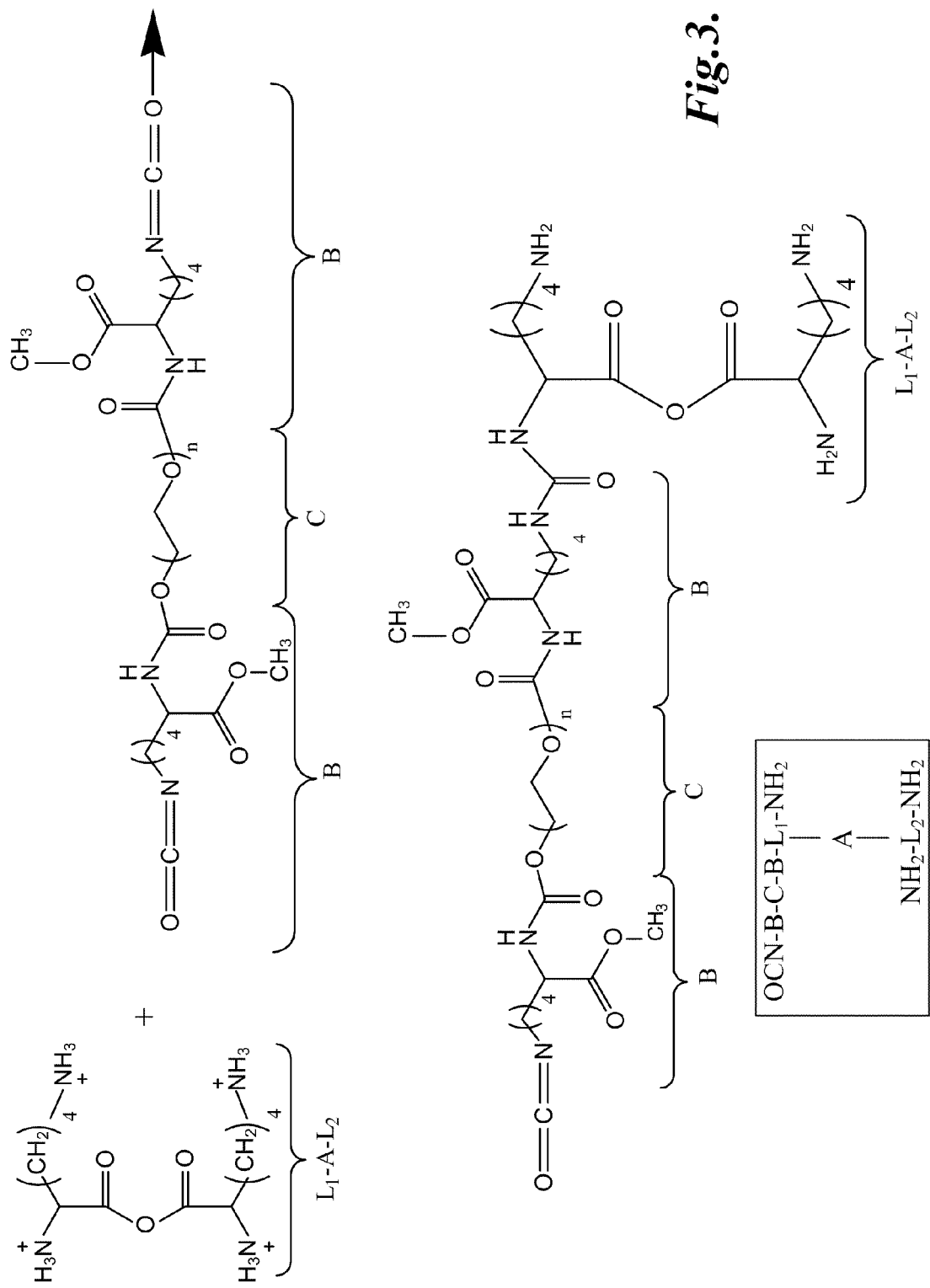
FIG. 3 schematically illustrates the synthesis of a compound useful in forming polymers of the invention.
Figure 4:
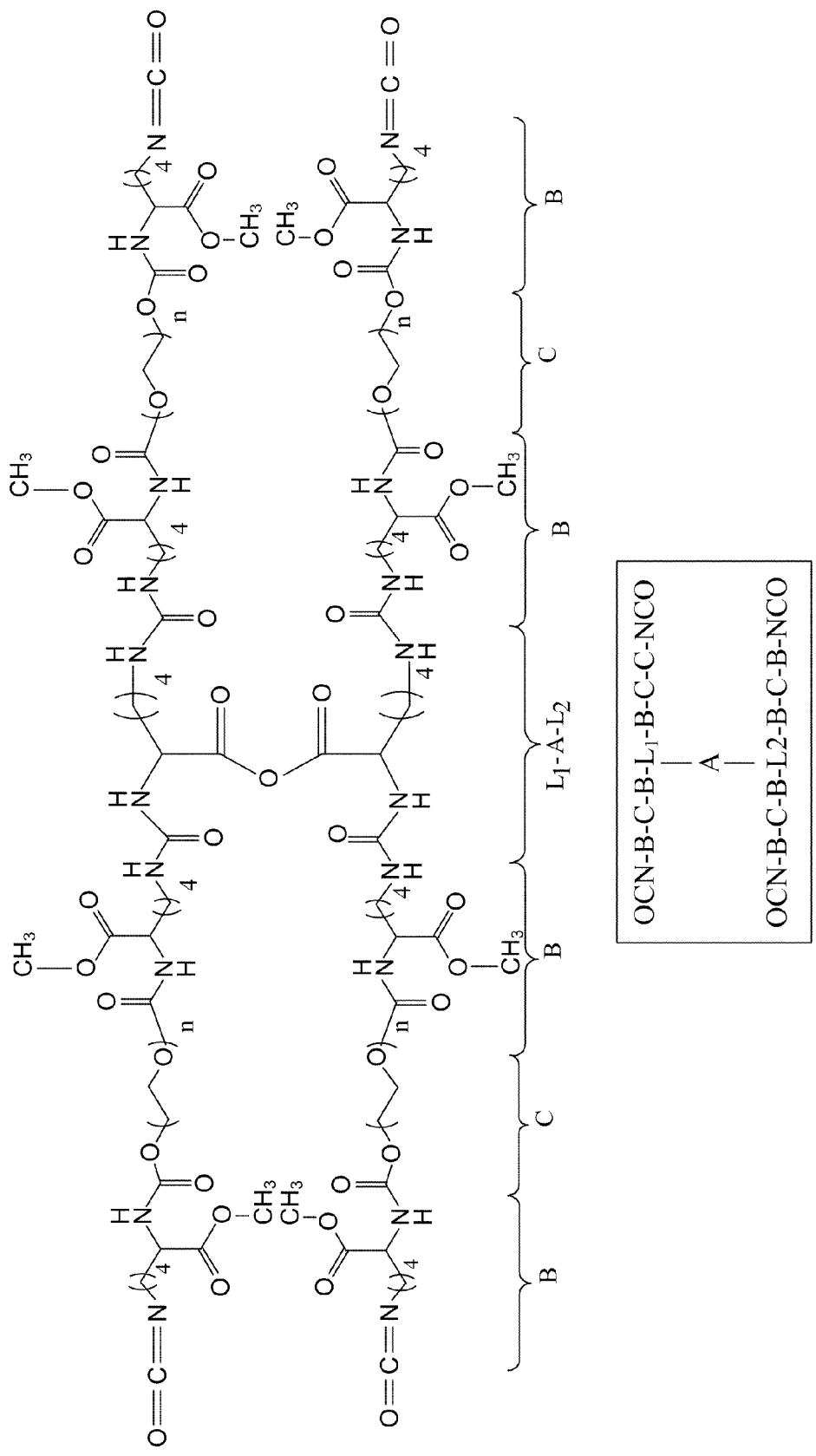
FIG. 4 illustrates a compound useful in forming polymers of the invention.

The preparation of a compound useful in making representative crosslinkable polymers of the invention, where the diisocyanate is lysine diisocyanate, the diol is a PEG, and the DAAA is a dilysine anhydride, is illustrated schematically in FIG. 3 and described in Example 1. While lysine diisocyanate is illustrated in FIG. 3 as formed by reaction with the isocyanate group derived from the α-amino group of lysine, it will be appreciated that lysine (and other diisocyanate compounds) can be formed by reaction with the isocyanate group derived from the amino group of the lysine (or other suitable amino acid) side chain groups (i.e., other regioisomers). In FIG. 3A, $L_1$-A-$L_2$, is dilysine anhydride ($L_1$ and $L_2$ are both lysine). As noted above, it will be appreciated that $L_1$ and $L_2$ need not be the same. For example, for highly crosslinked polymers of the invention, $L_1$ and $L_2$ can be independently selected from α-amino acids having side chains that include reactive groups (e.g., lysine, serine, threonine, tyrosine). In certain embodiments, $L_1$ is an α-amino acid having a side chain that includes a reactive group and $L_2$ is an amino acid having a side chain that does not include a reactive group. FIG. 4 illustrates the chemical structure of the intermediate illustrated in FIG. 3 that has reacted with three additional diisocyanate prepolymers (B—C—B).

Figure 5:
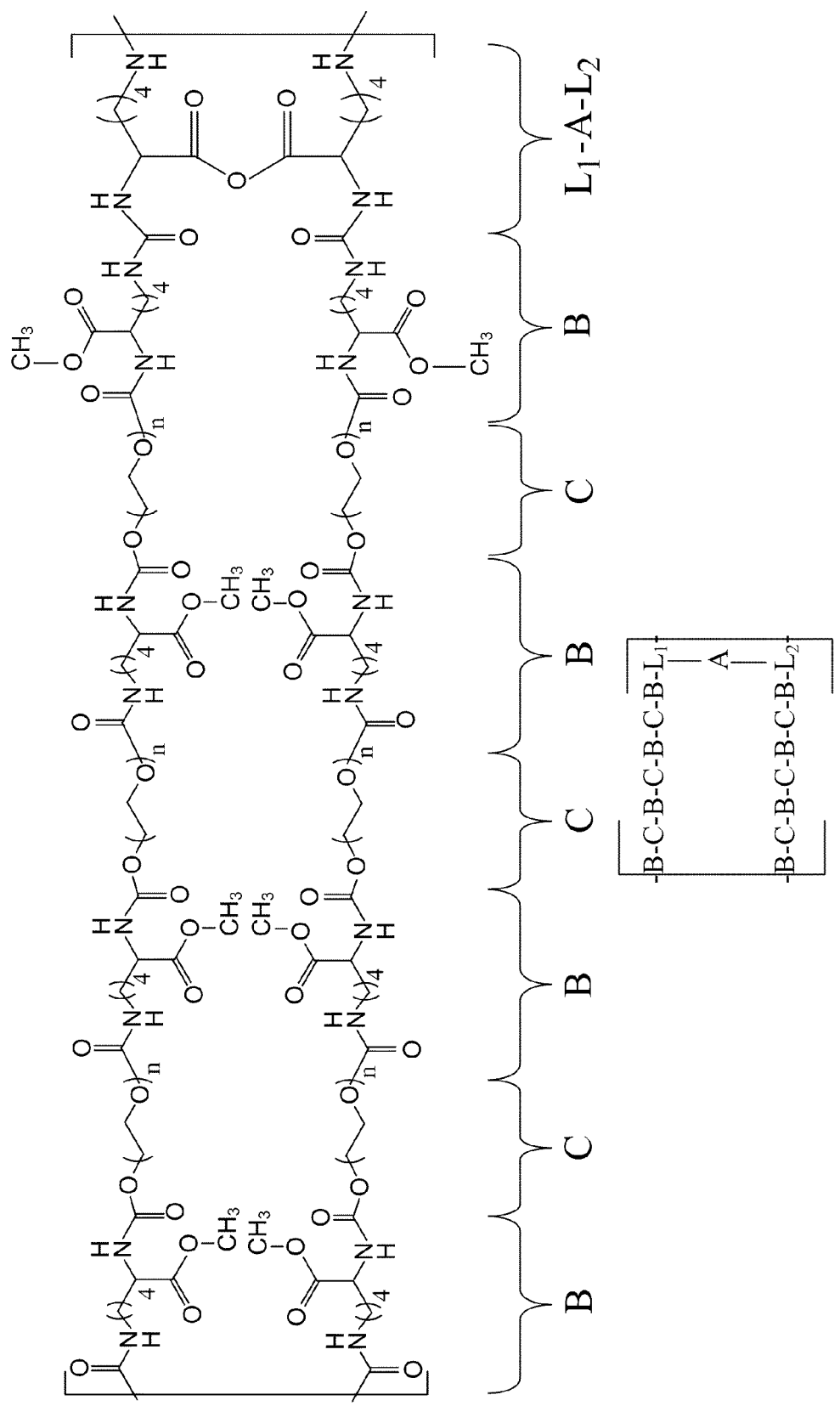
FIG. 5 illustrates a portion of a representative polymer of the invention.
Figure 6:
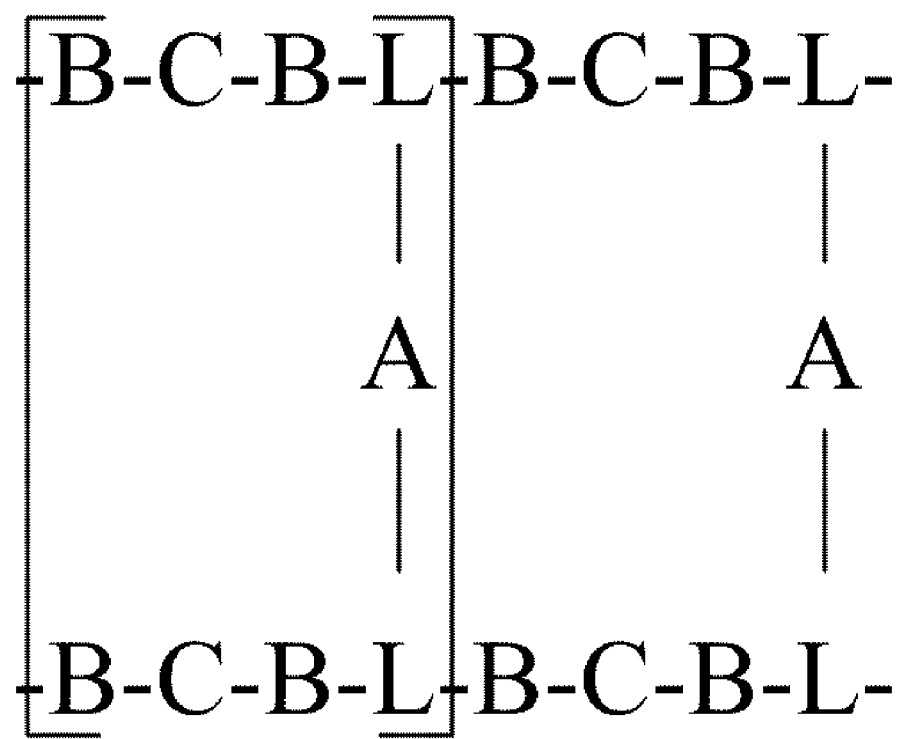
FIG. 6 illustrates a portion of a representative polymer of the invention.
Figure 7:
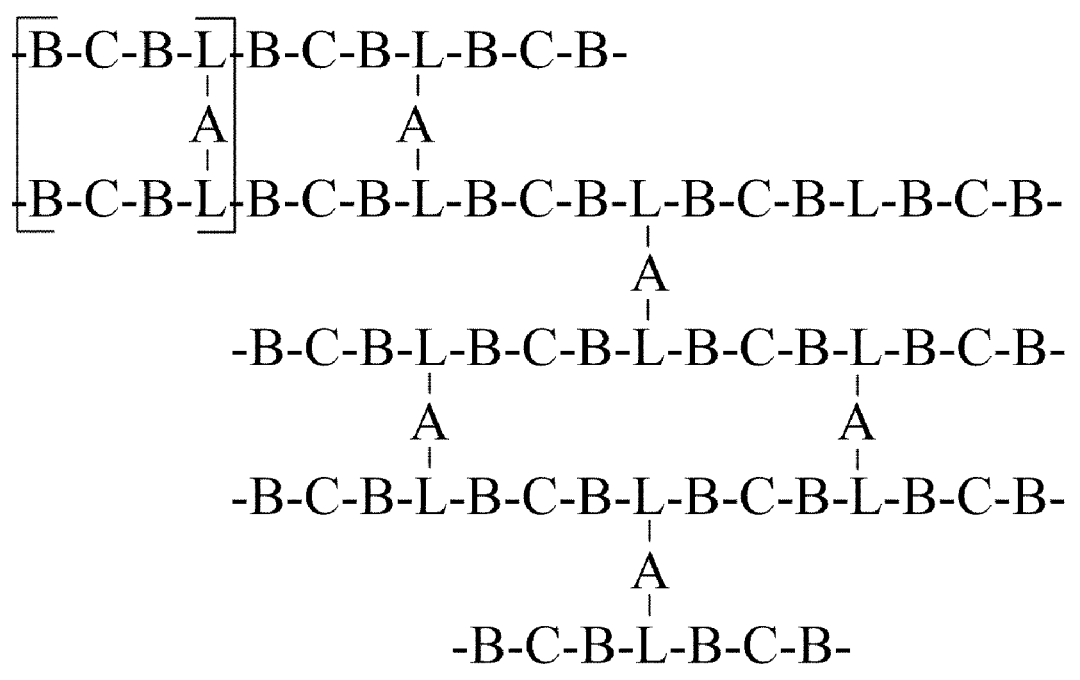

FIG. 5 illustrates a representative repeat unit of a polymer of the invention that is made from an extended prepolymer (B—C—B—C—B—C—B). FIG. 6 illustrates a portion of a crosslinked polymer structure of the invention. The crosslinked polymer structure has two repeating units $(BCBL)_2A$ and reactive isocyanate and amino groups useful for extending the polymer chain. A portion of a representative crosslinked polymer of the invention is illustrated schematically in FIG. 7. As illustrated in FIG. 7, the polymers of the invention can be highly crosslinked. The crosslinked polymers are formed using the diamine anhydrides to extend the polymer chains derived from the diisocyanate prepolymers. The crosslinking density and related physical properties (e.g., elasticity and hardness) can be controlled by varying the size of the prepolymer blocks (e.g., B—C—B or B—C—B—C—B—C—B). Smaller prepolymer blocks will result in a higher degree of crosslinking.

When forming polymers of the invention, how the reaction of the DAAA and prepolymer is terminated will determine the size and end-group functionality of the resulting polymer. Polymerization can be terminated by limiting the amount of DAAA and/or prepolymer reactants and allowing the reaction to proceed without additional quenching. The polymerization can also be quenched at a desired molecular weight with a suitable quencher. Compounds useful for quenching urea polymerization reactions are known to those of skill in the art. The end-group functionality of polymers of the invention can be tailored based on the compound used to terminate the polymerization reaction when forming the polymer.

In one aspect, the invention provides a polymer that includes repeating units having the structure:

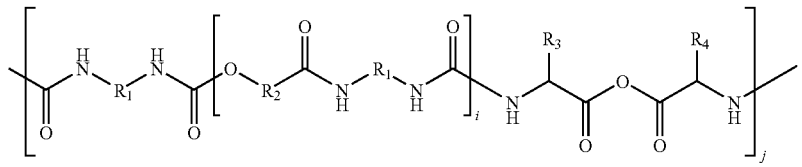

where $R_1$ is selected from —$(CH(COOCH_3)(CH_2)_4)$— and —$(CH_2)_k$—, where k is an integer from 1 to 5;

$R_2$ is selected from —$(CH_2CH_2O)_n$—, —$(C(=O)(CH_2)_5O)_n$—, —$(C(=O)CH(CH_3)O)_n$—, —$(C(=O)CH_2O)_n$—, and —$(C(=O)CH(CH_3)O)_n$—$(C(=O)CH_2O)_m$—, where n is an integer from 1 to 1000 and m is an integer from 1- to 1000;

$R_3$ and $R_4$ are independently selected from α-amino acid side chains and their stereoisomers;

i is an integer from 1 to 1000; and j is an integer from 1 to 1000.

As noted above, the polymers of the invention may include repeating units having different $R_1$ groups, different $R_2$ groups, and/or different $R_3$ and $R_4$ groups.

In one embodiment, at least one of $R_3$ and $R_4$ include an amino group, hydroxyl group, or phenol group capable of reacting with an isocyanate to form a covalent bond and the polymer is crosslinked through the reaction of the polymer repeating units with the group capable of reacting with an isocyanate.

In one embodiment, $R_1$ is —(CH(COOCH$_3$)(CH$_2$)$_4$)—.

In one embodiment, $R_2$ is —(CH$_2$CH$_2$O)$_n$—, and n is an integer from 1 to 1000.

In one aspect, the invention provides a polymer that includes repeating units having the structure:

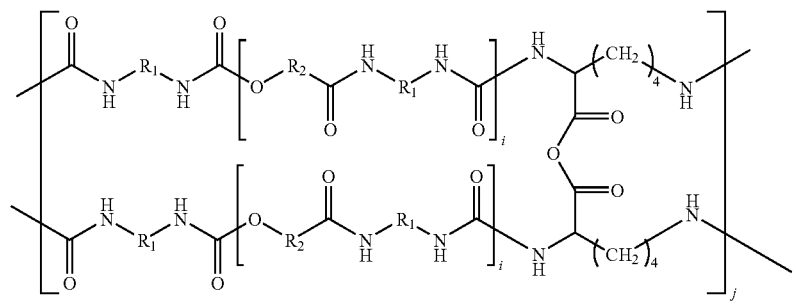

where $R_1$ is selected from —(CH(COOCH$_3$)(CH$_2$)$_4$)— and —(CH$_2$)$_k$—, where k is an integer from 1 to 5;

$R_2$ is selected from —(CH$_2$CH$_2$O)$_n$—, —(C(=O)(CH$_2$)$_5$O)$_n$—, —(C(=O)CH(CH$_3$)O)$_n$—, —(C(=O)CH$_2$O)$_n$—, and —(C(=O)CH(CH$_3$)O)$_n$—(C(=O)CH$_2$O)$_m$—, where n is an integer from 1 to 1000 and m is an integer from 1 to 1000;

i is an integer from 1 to 1000; and j is an integer from 1 to 1000.

As noted above, the polymers of the invention may include repeating units having different $R_1$ groups and/or different $R_2$ groups.

In one embodiment, $R_1$ is —(CH(COOCH$_3$)(CH$_2$)$_4$)—.

In one embodiment, $R_2$ is —(CH$_2$CH$_2$O)$_n$—, and n=1-1000.

Physical properties of polymers of the invention include biocompatibility, biodegradability, biotolerability, and mechanical properties. Because biodegradation typically occurs at the anhydride linkage, the rate at which the polymer biodegrades will be determined by the number of anhydride linkages. Hydrophobic amino acids forming the DAAA will also slow degradation via hydrolysis. Additionally, adding coats of other biocompatible polymers on polymers of the invention will help control their morphology and biodegradation rates.

The hydrophobicity of the polymers of the invention can be tailored by incorporating hydrophobic or hydrophilic amino acids (e.g., as L groups) and diisocyanates (e.g., as B groups). The uptake of biologically active materials (e.g., proteins) by the polymers can be similarly controlled.

Polymers of invention are useful in tissue engineering, organ regeneration, and related applications. Because the polymers of the invention include amino acid building blocks coupled to biocompatible prepolymers, both the polymers and their biological degradation products are biotolerable and will help to minimize or otherwise prevent the inflammatory or foreign body responses that occur upon degradation in the body. In one aspect, the invention provides a method for repairing biological tissue comprising applying a polymer of the invention to a wound in need thereof.

In one aspect, the invention provides a biodegradable scaffold for soft tissue engineering including a polymer of the invention.

In one embodiment, the scaffold includes a material selected from a gene, a protein, a growth factor, and an antibiotic.

Polymers of the invention are not restricted to tissue engineering applications. The polymers can also be used, for example, in applications calling for bioconjugates, where the polymer is conjugated to small organic molecules, nucleic acids, and polypeptides, including growth factors (e.g., through a lysine amino group). The polymers can also be used as a matrix for the development of novel biocomposites materials for various in vivo or in vitro applications or as carriers for drug delivery applications.

In another aspect of the invention provides polymers derived from amino acids and that have Formulas IA and IB:

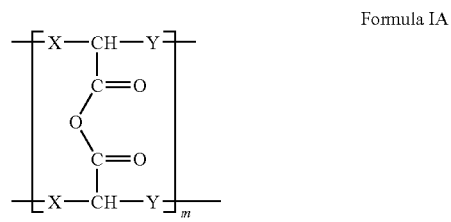

Formula IA where:

X is

—NHCONH(CH$_2$)$_4$CH(COOCH$_3$)NHCO(OCH$_2$CH$_2$)$_n$OCONHCH(COOCH$_3$)(CH$_2$)$_4$NH—; and Y is selected from —(CH$_2$)$_{1-4}$CONHCONH(CH$_2$)$_4$CH(COOCH$_3$)NHCO(OCH$_2$CH$_2$)$_n$OCO—NHCH(COOCH$_3$)(CH$_2$)$_4$NH—, —(CH$_2$)$_{1-4}$CONH(CH$_2$)$_4$CH(COOCH$_3$)NHCO(OCH$_2$CH$_2$)$_n$OCO—NHCH(COOCH$_3$)(CH$_2$)$_4$NH—, —(CH$_2$)$_{1-4}$NHCONH(CH$_2$)$_4$CH(COOCH$_3$)NHCO(OCH$_2$CH$_2$)$_n$OCO—NHCH(COOCH$_3$)(CH$_2$)$_4$NH—, —(CH$_2$)$_{1-4}$OCONH(CH$_2$)$_4$CH(COOCH$_3$)NHCO(OCH$_2$CH$_2$)$_n$OCO—NHCH(COOCH$_3$)(CH$_2$)$_4$NH(CH$_2$)$_{0-2}$CH(CH$_3$)OCONH(CH$_2$)$_4$CH(COOCH$_3$)—NHCO(OCH$_2$CH$_2$)$_n$OCONHCH(COOCH$_3$)(CH$_2$)$_4$NH—, and —(CH$_2$)$_{1-4}$(C$_6$H$_4$)OCONH(CH$_2$)$_4$CH(COOCH$_3$)NHCO(OCH$_2$CH$_2$)$_n$OCO—NHCH(COOCH$_3$)(CH$_2$)$_4$NH—;

m is an integer from 1 to 1000; and
n is an integer from 1 to 1000; and

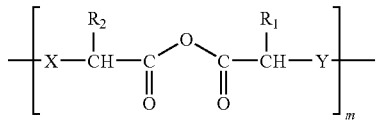

Formula IB where:
X and Y are independently selected from
—NHCONH(CH$_2$)$_4$CH(COOCH$_3$)NHCO(OCH$_2$CH$_2$)$_n$
OCO—NHCH(COOCH$_3$)(CH$_2$)$_4$NH— and
—NHCONH(CH$_2$)$_4$CH(COOCH$_3$)NHCO[O(CH$_2$)$_5$
C=O]$_n$OCH$_2$CH$_2$OCH$_2$CH$_2$O—[CO(CH$_2$)$_5$O]$_n$CONHCH
(COOCH$_3$)(CH$_2$)$_4$NH—;
m is an integer from 1 to 1000;
n is an integer from 1 to 20, and
R$_1$ and R$_2$ are independently selected from H, C$_{1-8}$ aliphatic, aromatic, or a combination thereof.

The resultant polymer may or may not be symmetrical across the anhydride group at the center and is synthesized from hydrochloride salt or isocyanate of amino acid anhydride that are linear, branched, or dendritic, having Formulas IIA or IIB:

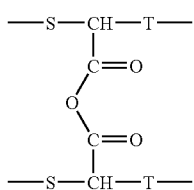

Formula IIA where:
S is selected from NH$_3$$^+$Cl$^-$ and N=C=O, and
T is selected from (CH$_2$)$_{1-4}$C=ONH$_2$,
(CH$_2$)$_{1-4}$NH$_3$$^+$Cl$^-$,
(CH$_2$)$_{1-4}$COOH,
(CH$_2$)$_{1-4}$OH, and
(CH$_2$)$_{1-4}$C$_6$H$_5$OH;
and

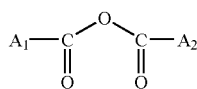

Formula IIB where A$_1$ and A$_2$ are independently selected from glycine, alanine, valine, leucine, isoleucine, methionine, phenylalanine, and proline, and the resultant anhydride and their hydrochloride salt or isocyanate derivative are either symmetrical or asymmetrical.

These amino acid anhydrides are coupled to prepolymer isocyanines of Formulas IIIA and IIIB:

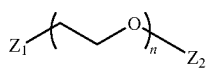

Formula IIIA where:
Z$_1$ is selected from OH, NH$_2$, COOH, NCO, and OCONH (COOCH$_3$)C$_4$H$_8$NCO;
Z$_2$ is selected from (CH$_2$)$_2$OH, (CH$_2$)$_2$NH$_2$, (CH$_2$)$_2$COOH, (CH$_2$)$_2$NCO, and (CH$_2$)$_2$OCONH(COOCH$_3$) C$_4$H$_8$NCO; and
n is an integer from 1 to 1000;
and

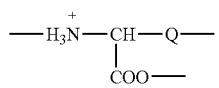

Formula IIIB where:
Z$_1$ is selected from H, CH$_2$NH$_2$, CH$_2$COOH, and CONH (COOCH$_3$)C$_4$H$_8$NCO;
Z$_2$ is selected from H, (CH$_2$)$_{1-2}$OH, (CH$_2$)$_{1-2}$NH$_2$, (CH$_2$)$_{1-2}$COOH, (CH$_2$)$_{1-2}$NCO, and (CH$_2$)$_{1-2}$OCONH(COOCH$_3$)C$_4$H$_8$NCO;
m is an integer from 1 to 5; and
n is an integer from 1 to 1000.

Compounds having Formulas IIA and IIB are synthesized from amino acids having Formula IV and biocompatible oligomers having Formula IIIA and IIIB are synthesized from compounds having Formulas VA and VB:

$$—H_3\overset{+}{N}—CH—Q—$$
$$\phantom{—H_3\overset{+}{N}—}\underset{COO—}{|}$$

Formula IV where:
Q is selected from (CH$_2$)$_{1-5}$, (CH$_2$)$_{1-5}$NH$_3$$^+$Cl$^-$ (linear or branched), (CH$_2$)$_{1-5}$COOH, (CH$_2$)$_{1-5}$OH, (CH$_2$)$_{1-4}$ C=ONH$_2$, C$_6$H$_5$, (CH$_2$)$_{1-4}$C$_6$H$_5$, and (CH$_2$)$_{1-4}$C$_6$H$_4$OH;
and

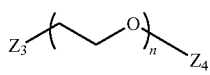

Formula VA where:
Z$_3$ is OH;
Z$_4$ is (CH$_2$)$_2$OH; and
n is an integer from 1 to 1000; and

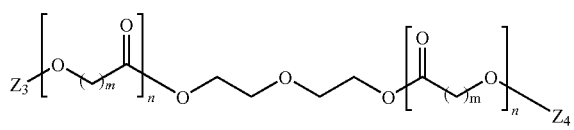

Formula VB where:
Z$_3$ and Z$_4$ are independently selected from H, (CH$_2$)$_{1-20}$H, (CH$_2$)$_{1-2}$NH$_2$, (CH$_2$)$_{1-2}$COOH, (CH$_2$)$_{1-2}$NCO, and (CH$_2$)$_{1-20}$ CONH(COOCH$_3$)C$_4$H$_8$NCO;
m is an integer from 1 to 5; and
n is an integer from 1 to 1000.

The following examples are provided for the purpose of illustrating, not limiting, the invention.

EXAMPLES

Example 1

Figure 8:
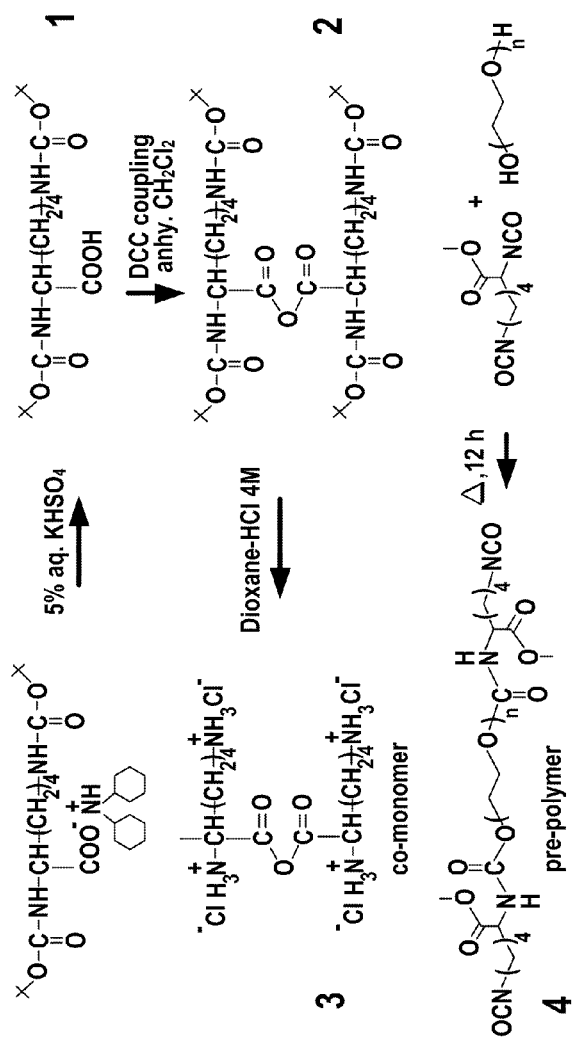
FIG. 8 schematically illustrates the synthesis of a representative polymer of the invention.
Figure 8:
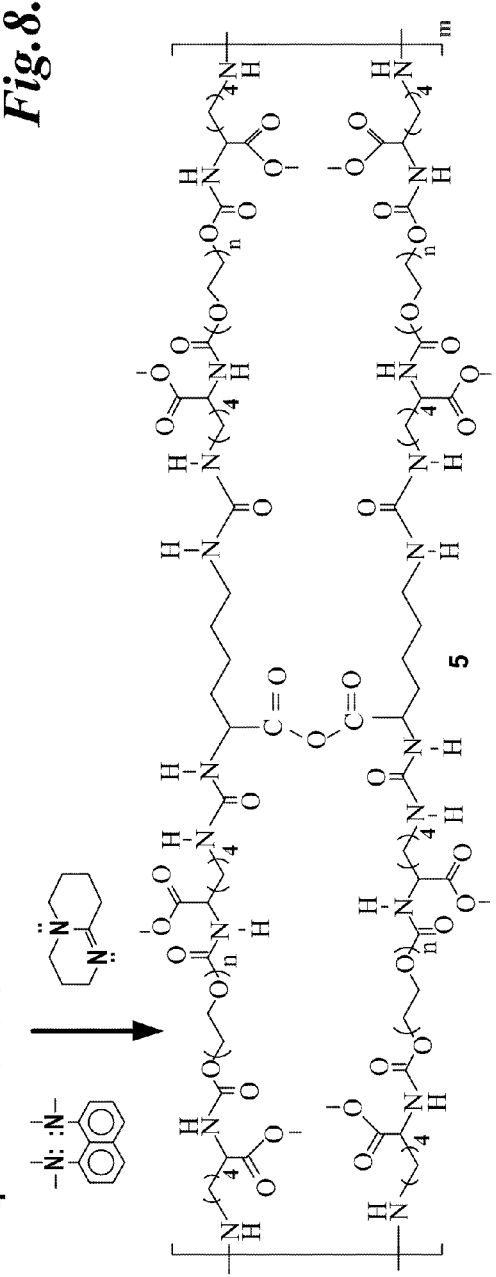

The Preparation and Characterization of a Representative Crosslinked Polymer A multifunctional poly(ethylene glycol) (PEG)-lysine anhydride polymer of the invention was synthesized from low molecular weight PEG (~1000 g/mol) and two lysine derivatives, as schematically illustrated in FIG. 8. Reaction of a prepolymer PEG-lysine diisocyanate and co-monomer dil-ysine anhydride produced the polymer. The number of degradation sites in the polymer can be controlled by varying the lysine anhydride repeat units. All steps involved in the synthesis were carried out at room temperature under inert and anhydrous conditions generated using argon and nitrogen gas. All intermediates at each step of the synthesis were isolated and characterized using nuclear magnetic resonance (NMR) and Fourier transform infrared spectroscopy (FTIR). The molecular weight of the polymer was determined by gel permeation chromatography (GPC). The polymer is hydrophilic, exhibits low cytotoxicity, and has useful elastic properties. These properties are desirable in several biomedical applications, including tissue engineering for soft tissue reconstruction.

Materials. Di(t-BOC) lysine-dicyclohexylamine (DCHA) was purchased from Novabiochem, EMD Biosciences, Inc. (San Diego, Calif.). Acetonitrile, dichloromethane, methanol, ethyl ether, pet ether, sodium sulfate, and sodium hydroxide were obtained from Fisher Scientific (Fair Lawn, N.J.). Dicyclohexyl carbodiimide (DCC) was obtained from the Fluka Chemical Corp. (Ronkonkoma, N.Y.). Dioxane and dioxane-HCl (4.0M) were procured from Sigma-Aldrich. $CD_3CN$ and $CDCl_3$ were procured through Cambridge Isotope Labs, Inc. (Andover, Mass.). Lysine diisocyanate was donated by Kyowa Hakko Co. Ltd., Japan.

Synthesis of Di(t-Boc)Lysine (1). Di(t-BOC) lysine-DCHA (1.000 g, 1.895 mmol) was dissolved in anhydrous dichloromethane (DCM) (15 mL), and washed (5×20 mL) with $KHSO_4$ solution (5 wt % in $H_2O$, ~pH=2) using a separating funnel. The collected layers of DCM were dried over anhydrous $MgSO_4$ to remove water traces and then transferred, rinsed, and filtered off with DCM (15 mL). The DCM from the organic layer was evaporated to give Di(t-BOC) lysine-COOH and the product was further dried under high vacuum to remove solvent traces and was stored at −20° C. The average yield using $KHSO_4$ treatment was above 93%.

Synthesis of Di(t-Boc)Lysine Anhydride (2). Anhydrous dichloromethane (DCM) (22 mL) and Di(t-BOC) lysine (2.487 g, 7.2 mM) were added to a 100 mL capacity round bottomed flask (RB) containing a magnetic stir bar and maintained under $N_2$ atmosphere. In a separate RB under $N_2$ atmosphere, dicyclohexylcarbodiimide (0.894 g, 4.333 mM) was dissolved in anhydrous DCM (12 mL) and the flask was chilled for 2 min in ice bath. The DCC solution was transferred using a syringe to the RB containing Di(t-BOC) lysine solution, and the flask was set to stir for 15 min at room temperature then cooled to 0° C. in an ice bath and left for 15 min of additional stirring. The product was stored at −20° C. for 90 min to allow complete precipitation of dicyclohexyl urea byproduct, which was then filtered off and rinsed with fresh chilled DCM. The filtrate was evaporated until a highly viscous solution was left behind. The product was crystallized using a minimal amount of 1:1 (diethyl ether: petroleum ether). Repeated crystallization were used to purify the product. White semi-crystalline product (Di(t-BOC) lysine anhydride 2) was obtained upon recrystallization. This reaction yielded ~90% product.

Synthesis of Lysine Anhydride Hydrochloride (Co-monomer 3). Pre-dried precipitates of Di(t-BOC) lysine anhydride 2 (1.25 gm) were dissolved in anhydrous dioxane (15 mL) in a dry RB followed by drop-wise addition of anhydrous dioxane-HCl (4.0 M) until the precipitation of hydrochloride salt of lysine anhydride began. The reaction mixture was stirred for 2-3 h under nitrogen atmosphere. White precipitates of the hydrochloride salt of lysine anhydride were formed in good yield (~80%) and collected by decanting the solvent, performing fresh diethyl ether washes, and evaporating the remaining solvent evaporation using rotary evaporation under vacuum. The product was stored in a dry container around 4° C.

Synthesis of PEG-Lysine Diisocyanate (Prepolymer 4). PEG-1000 (50 ml) was added to a 100 ml round bottom flask and left overnight on a heating plate at 105° C. under high vacuum to remove all moisture. The flask was allowed to cool gradually to 60° C. Lysine diisocyanate (16.9 g) and 38.2 g of PEG-1000 were added to a separate RB flask maintained at 83° C. under inert atmosphere. The reaction mixture was stirred for 8-10 hours. The resulting product is PEG-lysine diisocyanate.

Synthesis of PEG-Lysine Anhydride (Polymer 5). A thoroughly dry, round-bottomed flask (RB-1), containing a suspension of the hydrochloride salt of lysine anhydride 3 (0.3 g, 0.72 mM) in 10 mL anhydrous acetonitrile, was placed in a liquid nitrogen bath. Simultaneously, proton sponge (N,N,N', N'-tetramethyl-1,8-naphthalenediamine) (1.2 g, 5.76 mM), separately dissolved in 7 mL of acetonitrile in RB-2, was added drop-wise to RB-1. At this stage, 3 remained insoluble in acetonitrile. As the reaction temperature approached −50° C., the reaction mixture in RB-1 solidified. A non-nucleophilic base, 1,8-diazabicyclo[5.4.0]undec-7-ene (DBU) (0.75 mL), was then added drop-wise until the reaction mixture in RB-1 dissolved to a clear solution. Maintaining this reaction mixture at −10° C., a previously prepared solution of prepolymer 4 (4.1 g, 2.88 mM) in 10 mL acetonitrile (RB-3) was then added drop-wise to RB-1 under uniform stirring and inert conditions.

Acetonitrile was used as the solvent in the polymerization step because both DBU and proton sponge are known to have the highest pKa values in this solvent (Ikeda, I.; Simazaki, Y.; Suzuki, K. *J. Appl. Polym. Sci.* 1991, 42, 2871; Wu, W.; Verkade, J. G. *ARKIVOC* 2004, 9, 88). Thus, in this reaction, a proton sponge was used as a non-nucleophilic base for the in-situ regeneration of the free amine groups of 3 and DBU served both as solvent and non-nucleophilic base (Ikeda, I.; Simazaki, Y.; Suzuki, K. *J. Appl. Polym. Sci.* 1991, 42, 2871; Wu, W.; Verkade, J. G. *ARKIVOC* 2004, 9, 88).

Following the addition of 4, the reaction mixture was maintained in a dry ice bath for 1 hour followed by continuous stirring at room temperature for 5 days. The resulting pale yellow viscous liquid polymer 5 was then precipitated in anhydrous diethyl ether under constant stirring. The precipitate was washed repeatedly with fresh diethyl ether and vacuum-dried overnight. The resulting yellow-colored polymer was soluble in several protic and aprotic solvents such as water, acetonitrile, dimethyl formamide, chloroform, dimethylsulfoxide, and tetrahydrofuran. The weight-average molecular weight of 5 determined by gel permeation chromatography (GPC) was found to be 82,000 Daltons.

Figure 9A:
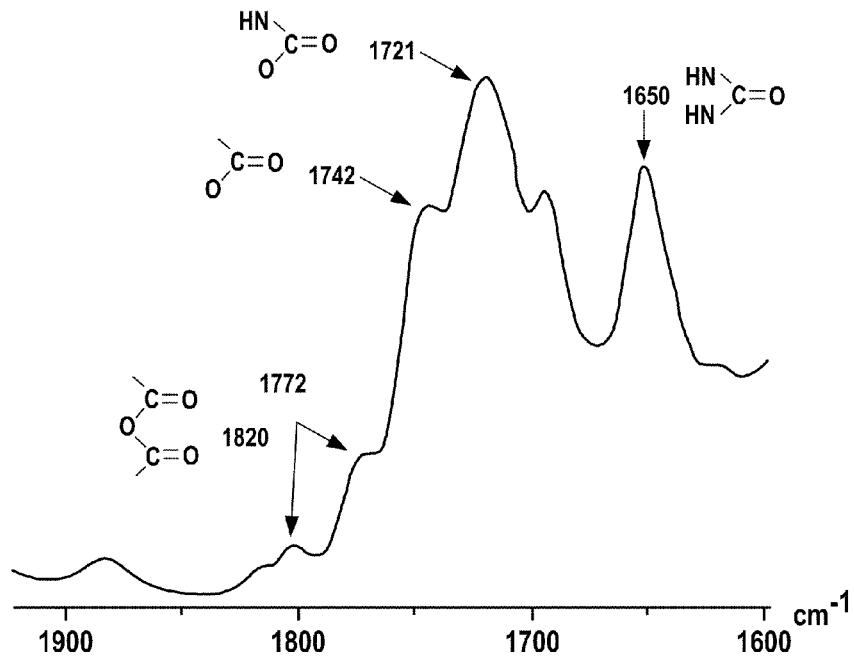
FIG. 9A is the FTIR spectrum of a representative polymer of the invention.

The structure of 5 was confirmed by FTIR, $^1H$ and $^{13}C$ NMR (750 MHz) spectroscopy. The FTIR spectrum of 5, illustrated in FIG. 9A, has peaks at wavenumbers $(cm^{-1})$ 1820, 1772, (anhydride), 1742 (ester), 1721 (carbamate), 1650 (urea), and 1040, 1110 (ether) respectively (*Structure Determination of Organic Compounds*; Pretsch, E.; Buhlmann, P.; Affloter, C. Eds.; Springer Publishers, New York, 2000). In the $^1$H NMR spectrum of 5, a distinct sharp peak at 3.6 ppm corresponding to PEG and the multiple peaks around 1.5 and 2.6 ppm corresponding to lysine anhydride repeating units were observed. The polymer structure was confirmed using $^{13}$C NMR.

Figure 9B:
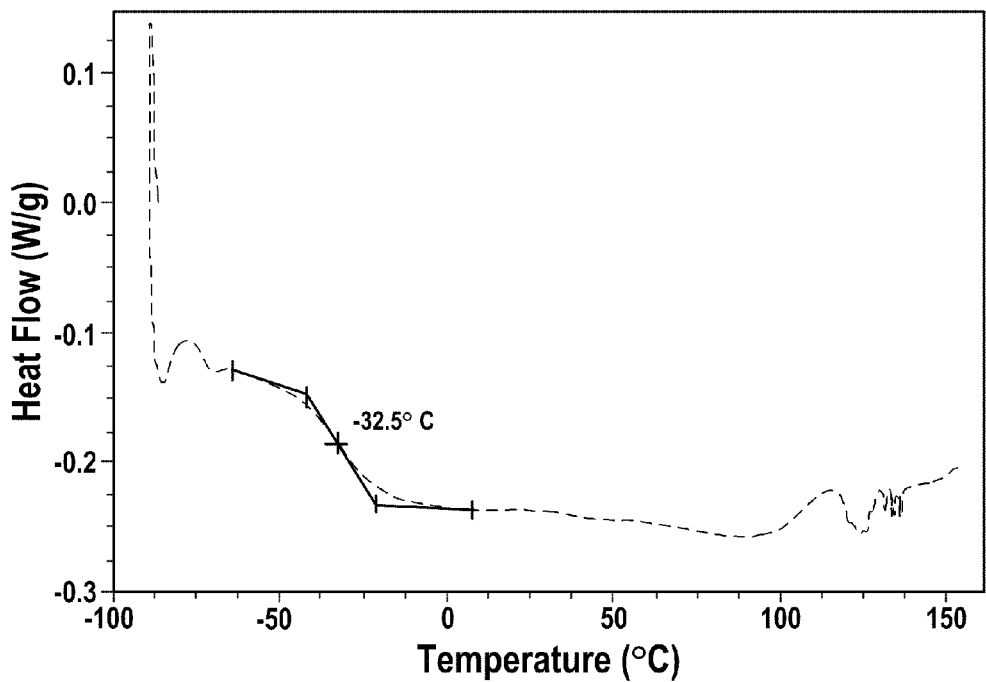
FIG. 9B is a DSC scan of a representative polymer of the invention.

Differential scanning calorimetry (DSC) measurements revealed a glass transition temperature ($T_g$) of −32° C., with no signs of melting ($T_m$) or crystallization ($T_c$), indicating the amorphous/semi-crystalline nature of this polymer (illustrated in FIG. 9B).

Figure 10:
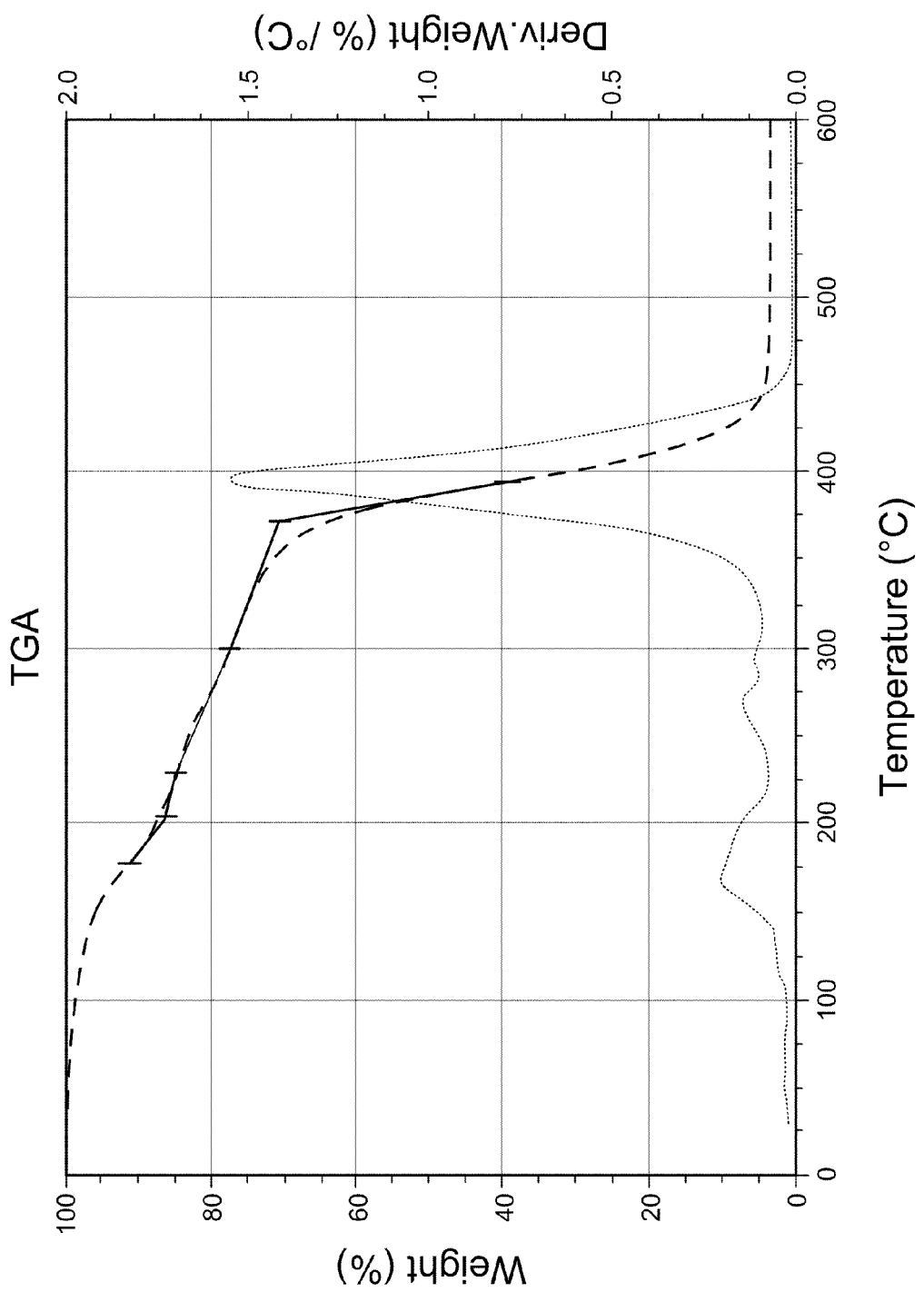
FIG. 10 is a TGA thermogram of a representative polymer of the invention.

TGA measurements of this polymer showed an initial decomposition temperature ($T_d$) of 203° C. and the maximum decomposition temperature ($T_{max}$) at 372° C. (illustrated in FIG. 10).

Physical characterization of solvent-cast films showed strain of up to 2000% elongation before break and a water contact angle of 22. When immersed in water, this elastomer exhibited a hydrogel characteristic followed by a linear weight-loss with time and eventual dissolution within two weeks. Breakdown of the polymer is believed to initiate from the hydrolysis of the lysine anhydride unit in the polymer backbone but may also be associated with soluble uncrosslinked chains.

Figure 11A:
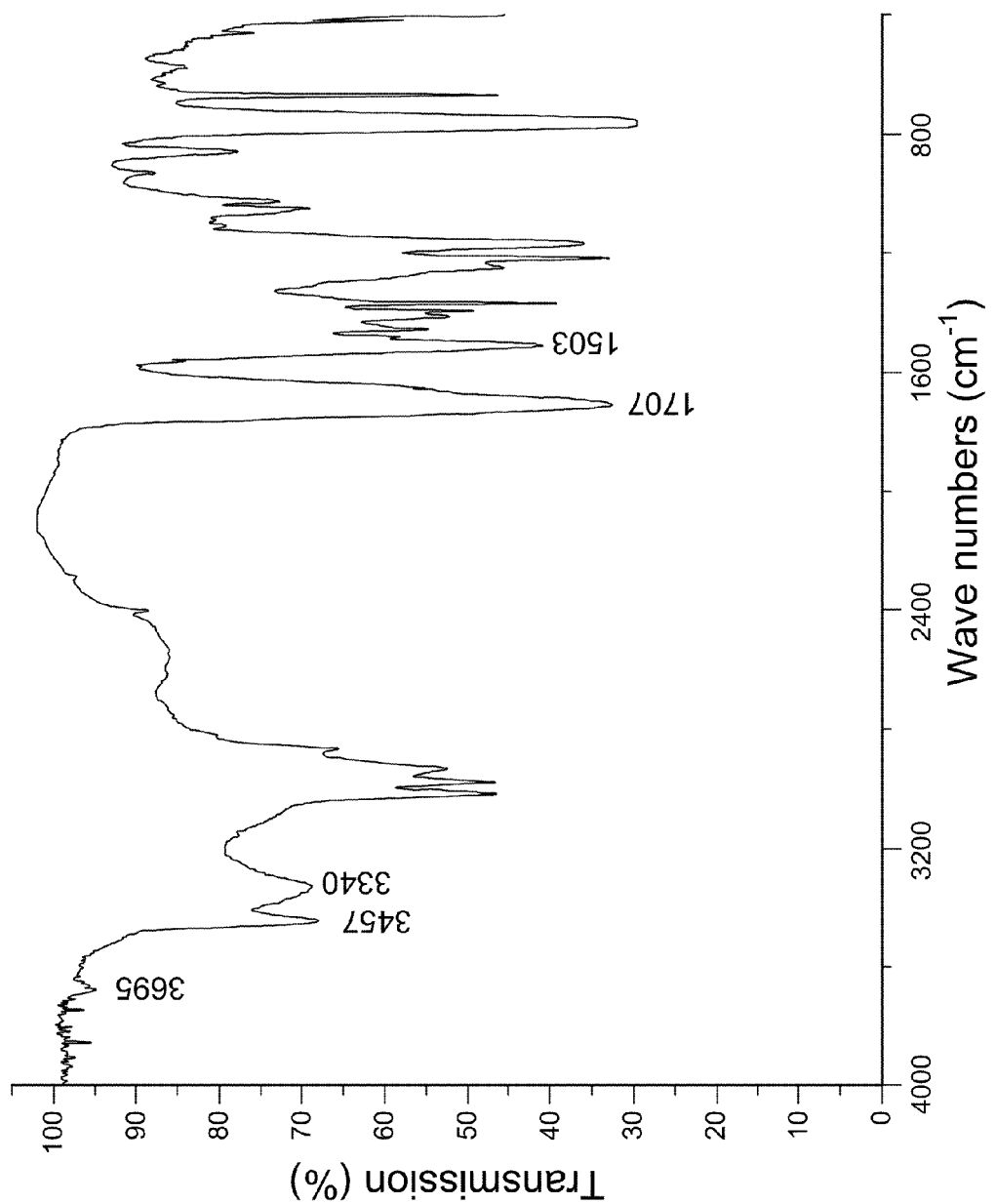
FIG. 11A is the FTIR spectrum of a starting material useful in forming polymers of the invention.
Figure 11B:
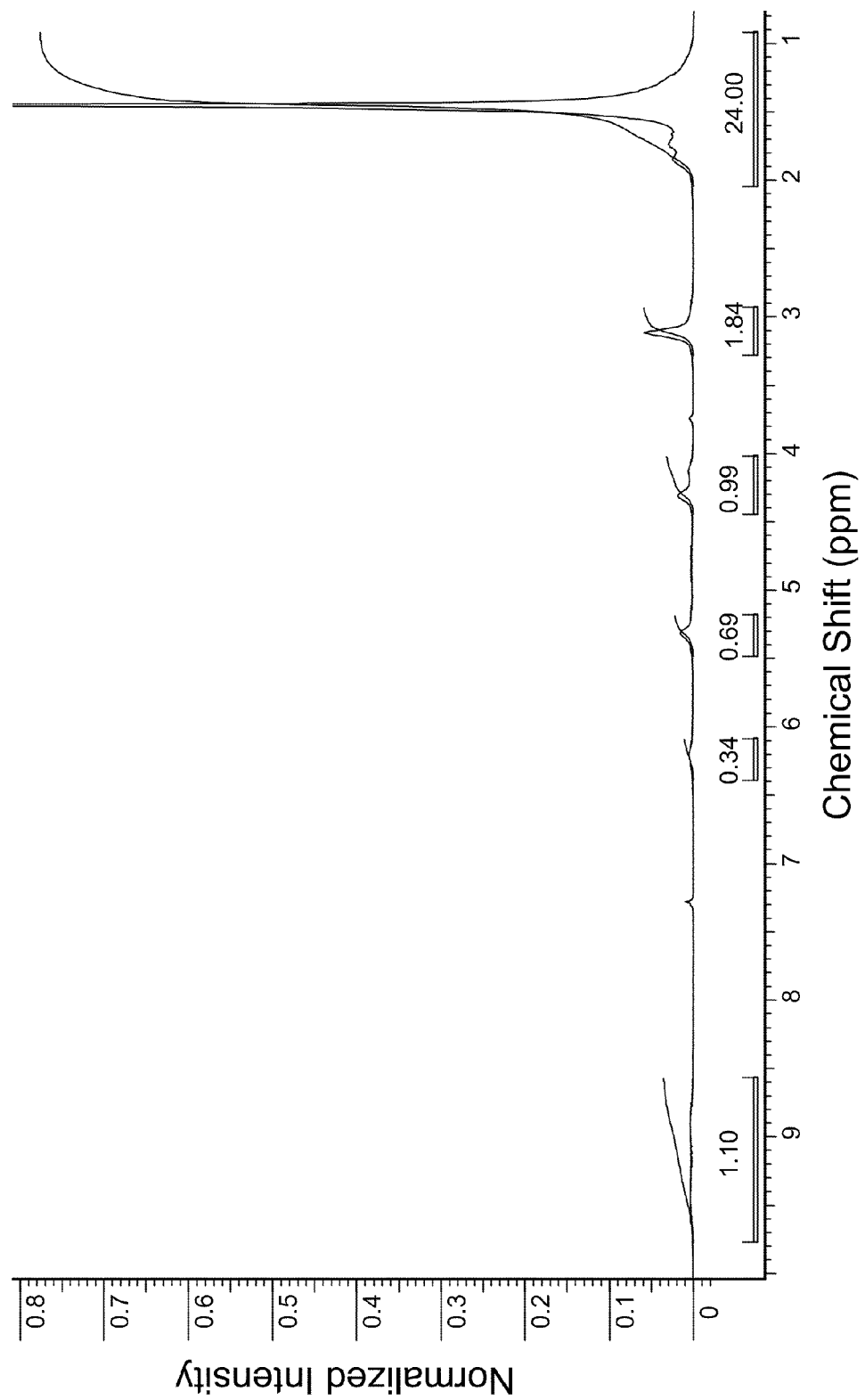
FIG. 11B is the $^1$H NMR spectrum of a starting material useful in forming polymers of the invention.
Figure 12A:
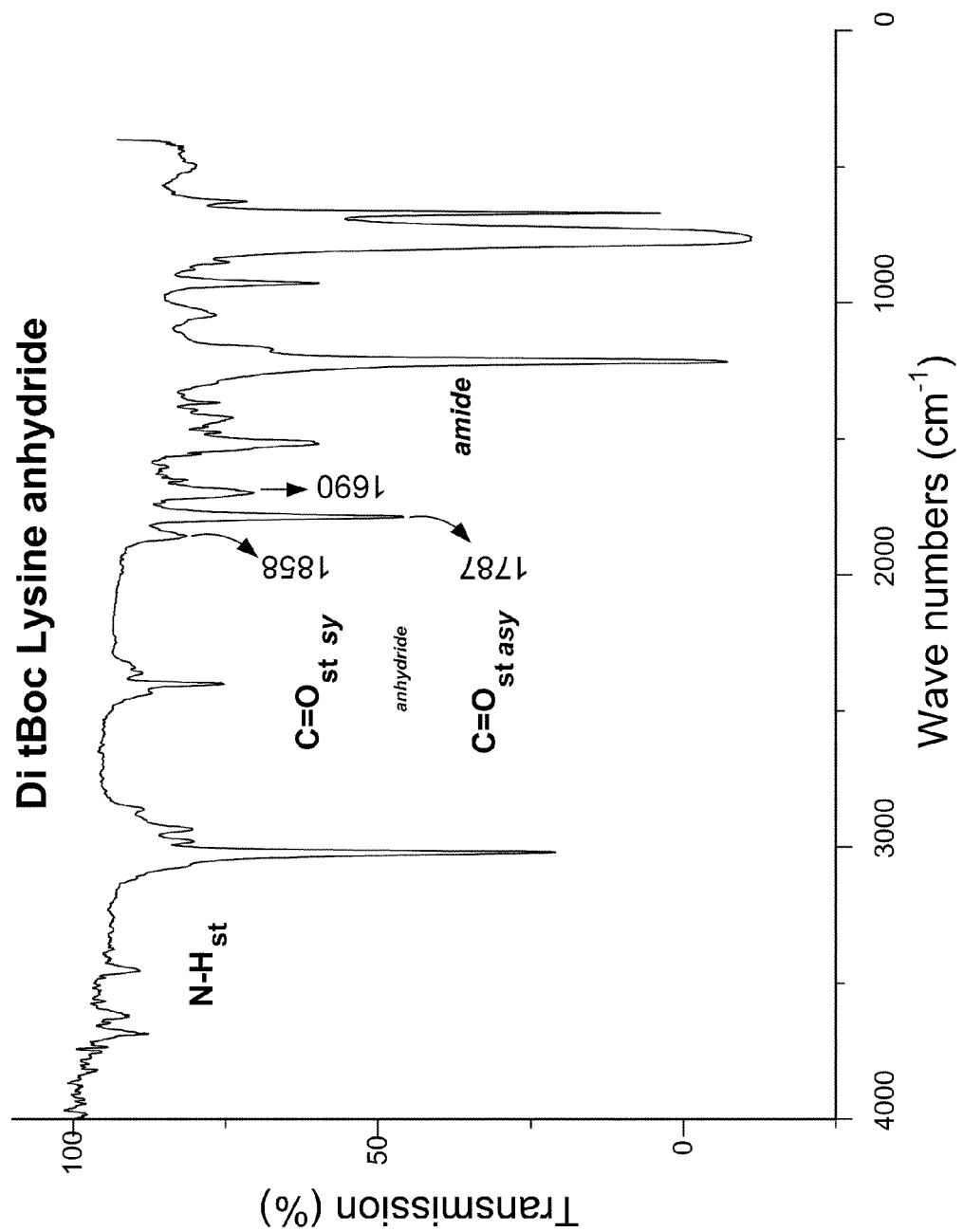
FIG. 12A is the FTIR spectrum of a starting material useful in forming polymers of the invention.
Figure 12B:
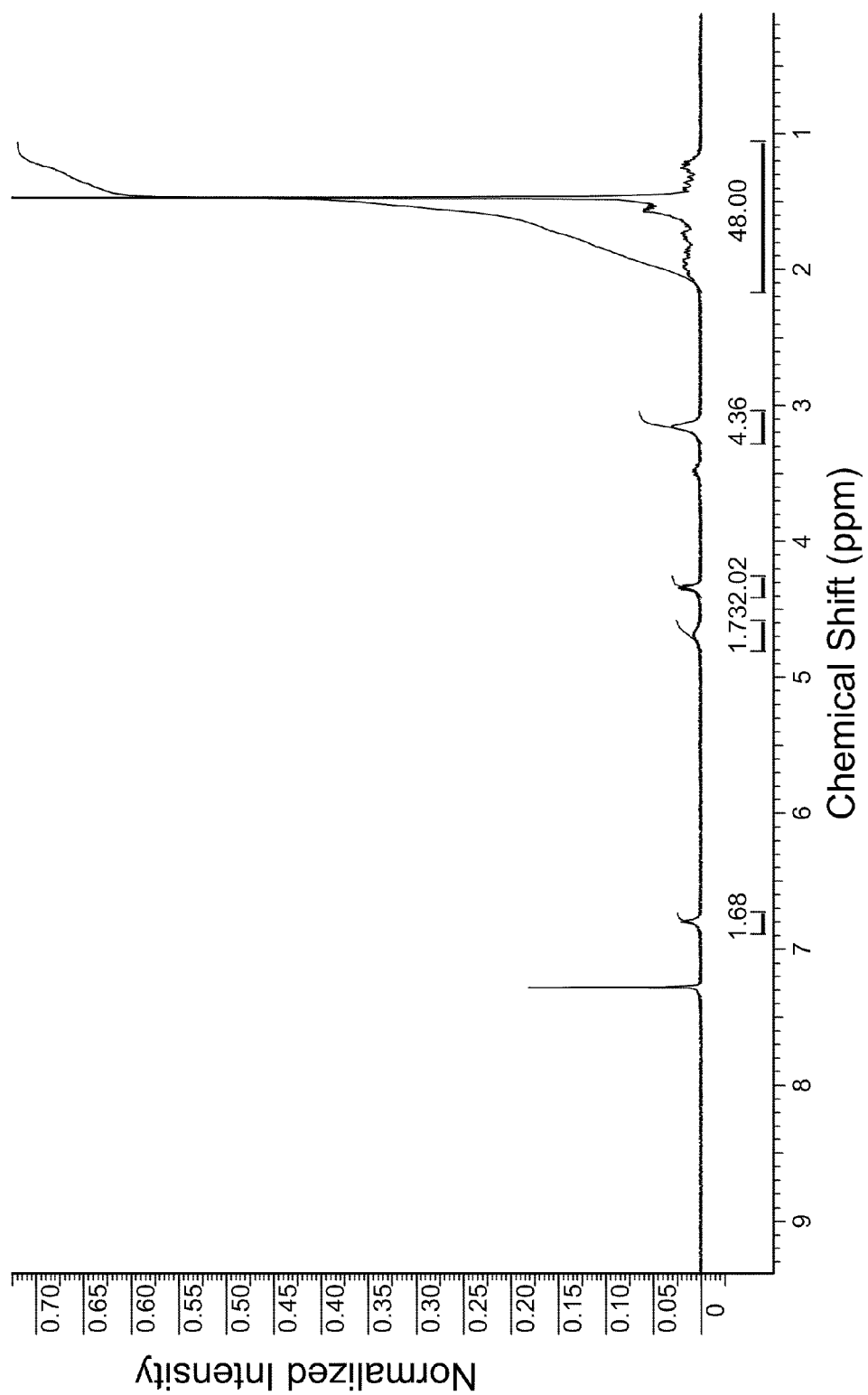
FIG. 12B is the $^1$H NMR spectrum of a starting material useful in forming polymers of the invention.
Figure 13A:
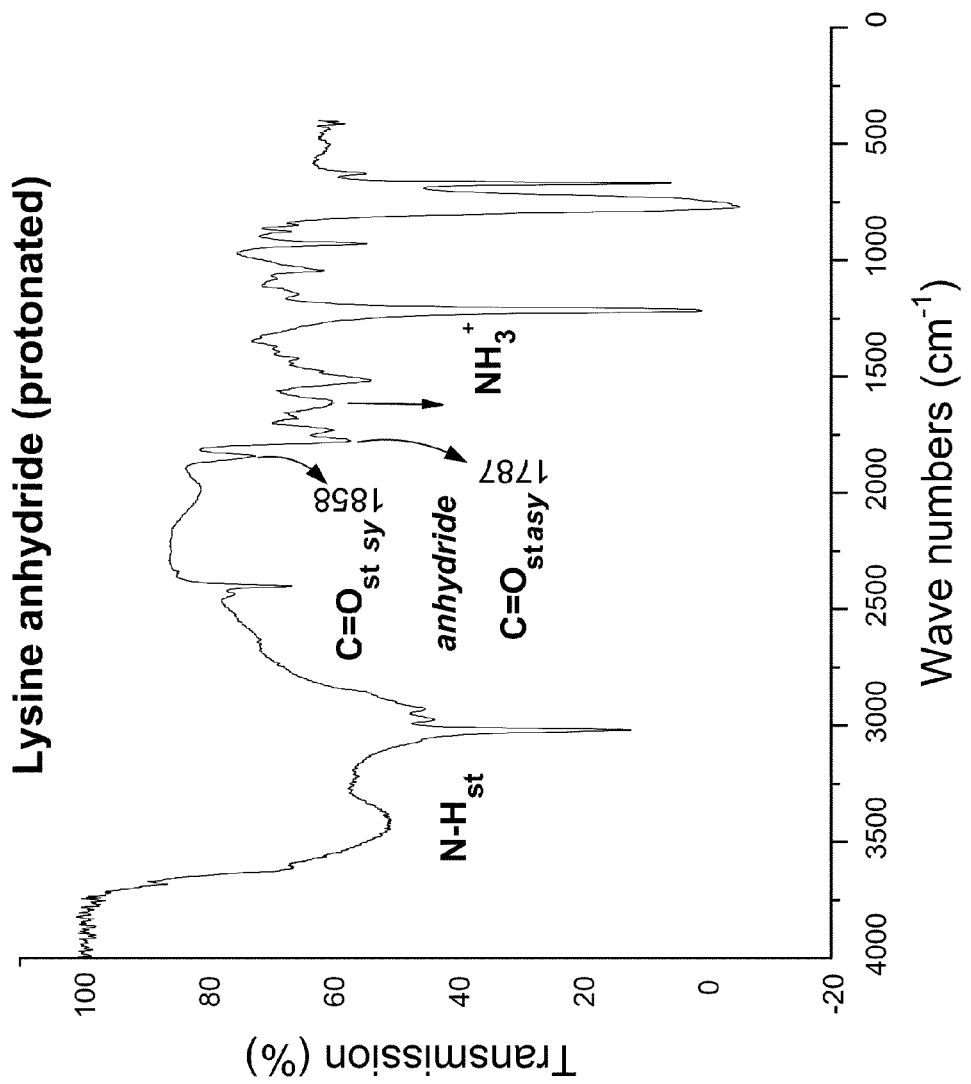
FIG. 13A is the FTIR spectrum of a starting material useful in forming polymers of the invention.
Figure 13B:
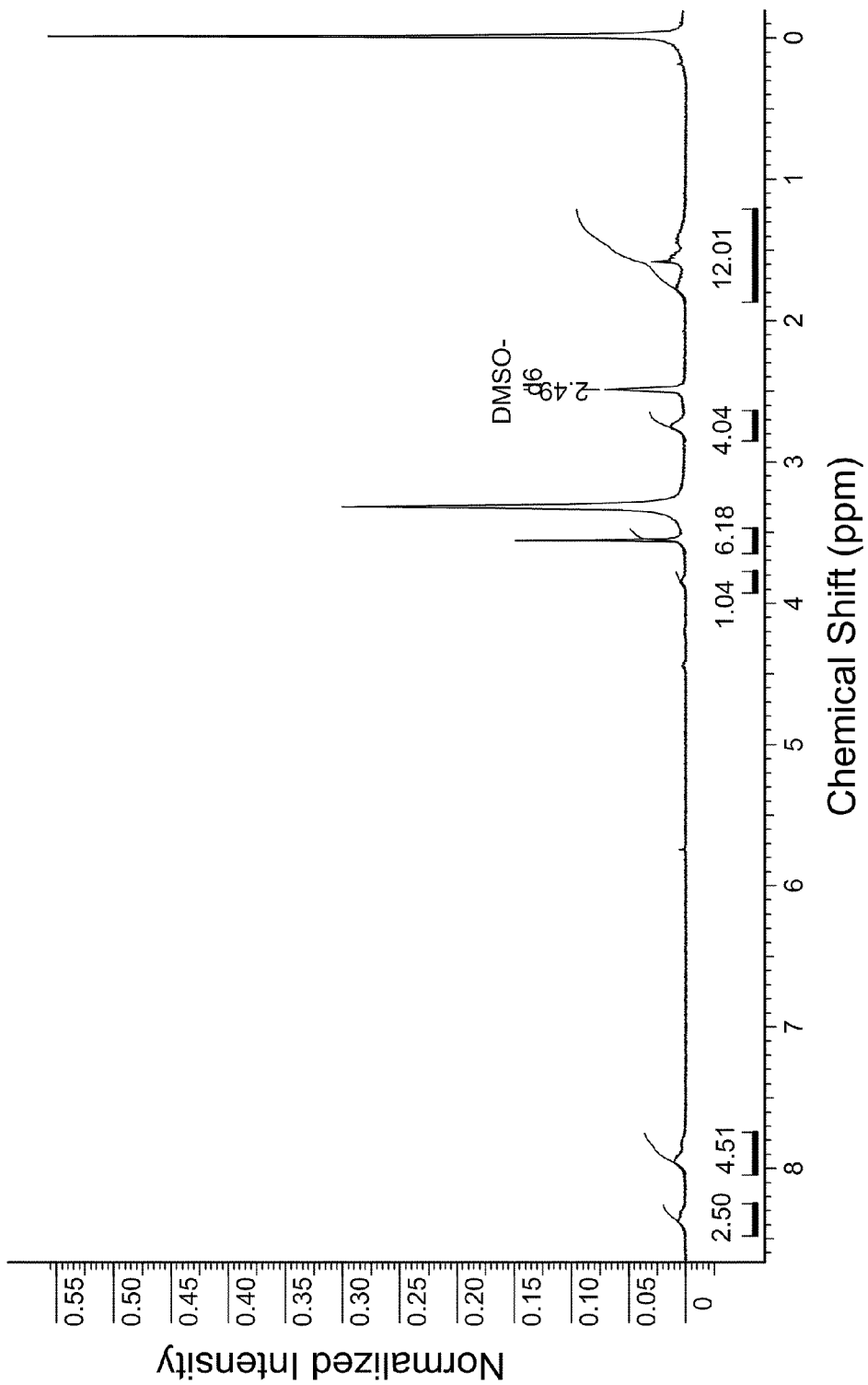
FIG. 13B is the $^1$H NMR spectrum of a starting material useful in forming polymers of the invention.

FIGS. 11A and 11B graphically illustrate the spectral patterns of di(t-boc)lysine. FIGS. 12A and 12B graphically illustrate the spectral patterns of di(t-boc)lysine anhydride. FIGS. 13A and 13B graphically illustrate sets forth the spectral patterns of lysine anhydride-hydrochloride.

Figure 14A:
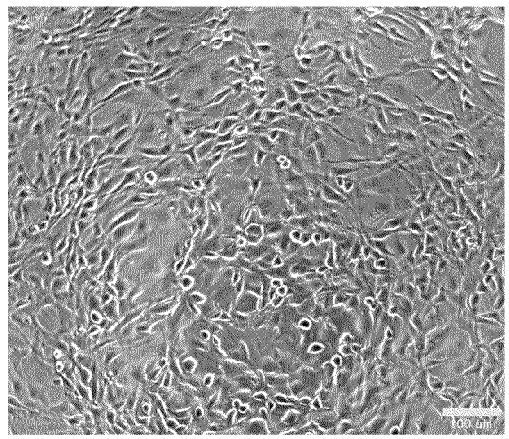
FIG. 14A-14C are micrograph images illustrating the results of fibroblast cultures on a representative polymer of the invention (14A) and two control media (14B and 14C)
Figure 14B:
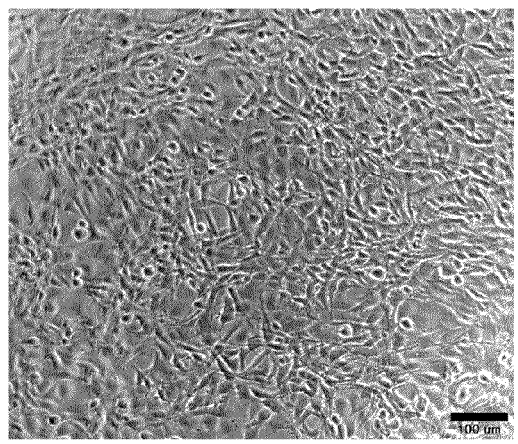
Figure 14C:
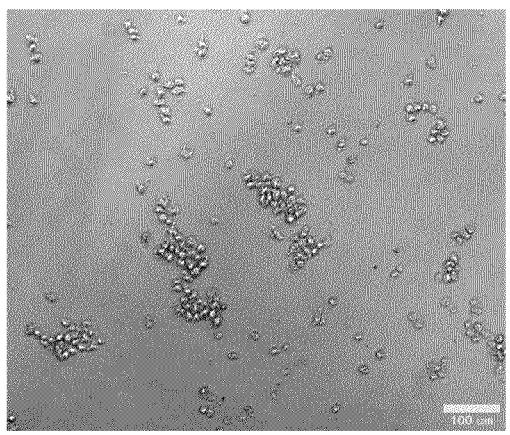

Cytotoxicity Tests. The soluble degradation products of 5 were exposed to NIH 3T3 fibroblasts for in vitro cytotoxicity assessment and were found to be non-toxic. FIG. 14 graphically illustrates NIH 3T3 fibroblasts at 48 hours under standard culture conditions (REF). After 48 hours, cell spreading and general morphology on 5 (FIG. 14A) appeared to be nearly identical to the tissue culture polystyrene (TCPS) control (FIG. 14B). The cells in the latex control (FIG. 14C) were distinguished by rounded clusters of non-viable cells.

Figure 15A:
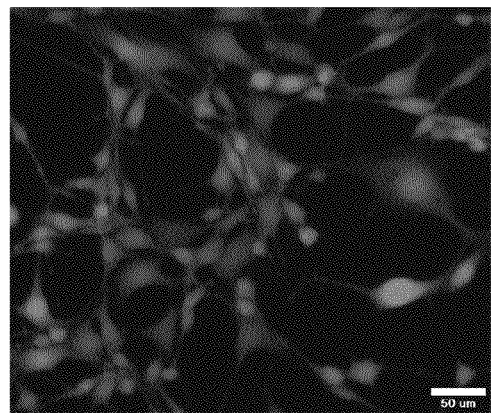
FIGS. 15A-15C are micrograph images illustrating the results of a LIVE/DEAD assay for cytotoxicity in the degradation products of a representative polymer of the invention (15A) and two control media (15B and 15C)
Figure 15B:
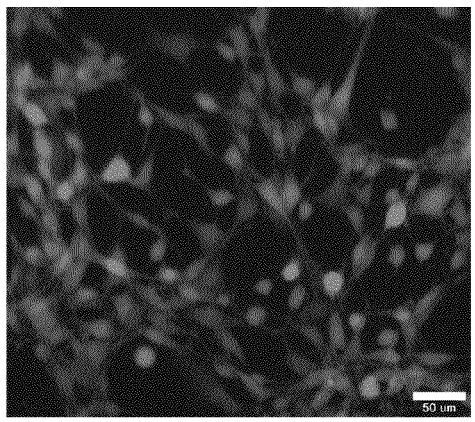
Figure 15C:
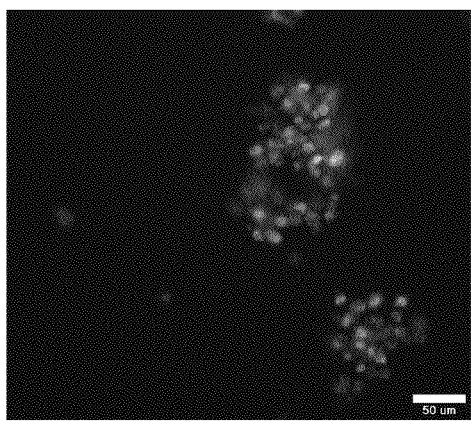

A LIVE/DEAD® assay was performed after 48 hours and the light microscope images depicted in FIG. 15 were obtained. All of the cells were alive in samples grown on media with degradation products of 5 (FIG. 15A) and TCPS control samples (FIG. 15B). Almost all of the cells in the latex control were dead (FIG. 15C).

Example 2

The Preparation and Characterization of Representative Linear Polymers

Figure 16:
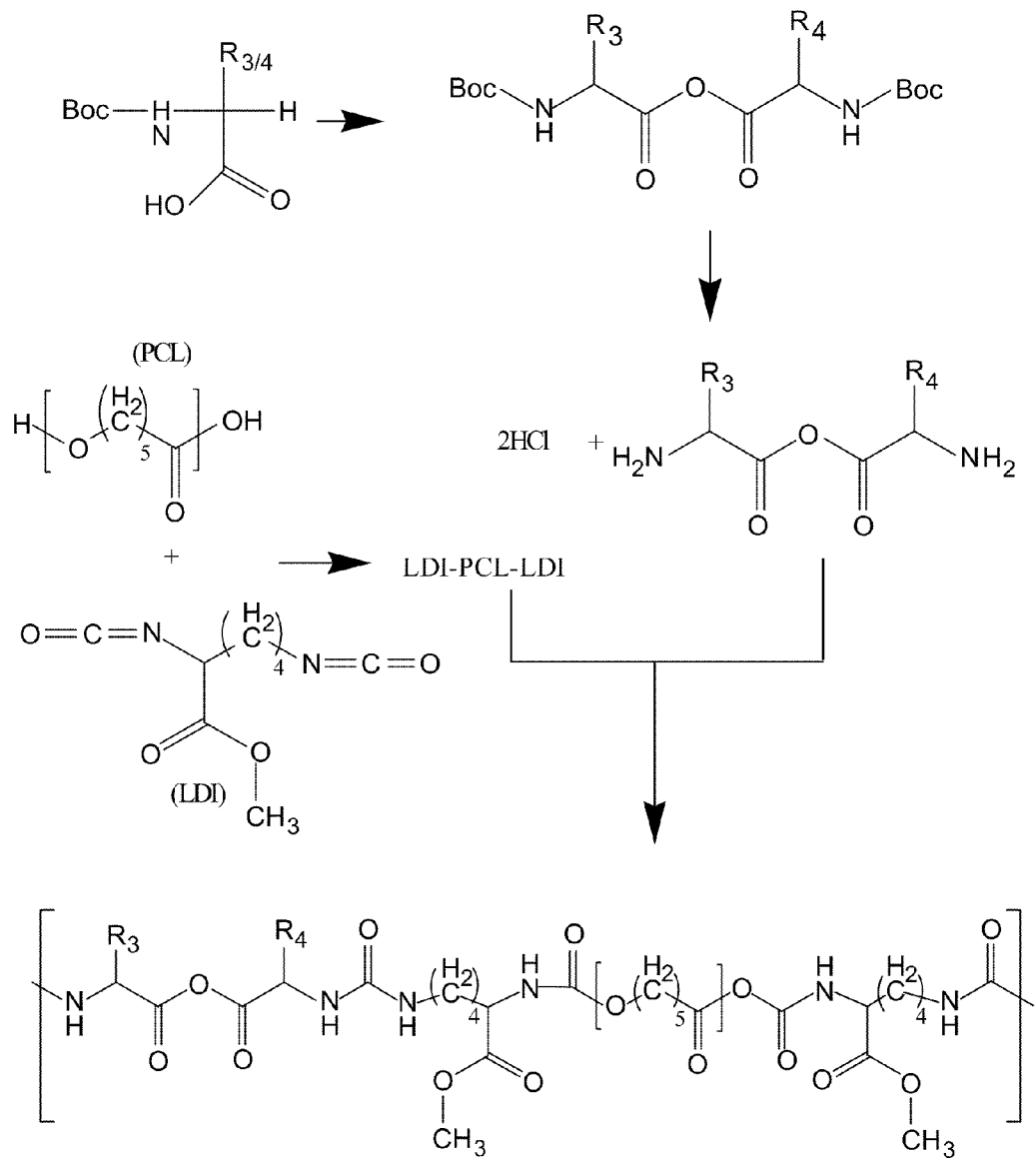
FIG. 16 schematically illustrates the synthesis of a representative polymer of the invention.

Linear amino acid anhydride polymers of the invention were prepared in a manner analogous to the procedure described above in Example 1. All intermediates at each step of the synthesis were isolated and characterized using nuclear magnetic resonance (NMR) and Fourier transform infrared spectroscopy (FTIR). The molecular weights of the polymers were determined by gel permeation chromatography (GPC). The preparation of the linear polymers of the invention is illustrated schematically in FIG. 16.

Amino Acid Anhydrides. The amino acids anhydrides were prepared by the procedure described above in Example 1. Representative amino acid anhydrides included anhydrides prepared from leucine and glycine, valine and alanine, alanine and alanine, and lysine and alanine.

PCL-Lysine Diisocyanate. A 100 ml round bottom flask containing 50 ml of polycaprolactone diol-1000 (PCL diol) was dried under high vacuum overnight on at heating plate at 90° C. to remove moisture. The flask was allowed to cool gradually to 60° C. Next, 3.0 mole equivalent of lysine diisocyanate to a separate round bottom flask maintained at 83 C, and under inert atmosphere, 1.0 mole equivalent of PCL diol (1000 Daltons) was added. The reaction mixture was stirred for 8-10 hrs. The resulting product is PCL-lysine diisocyanate.

Linear polymers. The linear polymers were prepared by reaction of the amino acid anhydride (leucine/glycine, valine/alanine, alanine/alanine) with PCL-lysine diisocyanate by the procedure described above in Example 1.

Lysine/Alanine Anhydride Polymer. The polymer prepared from the lysine/alanine anhydride is a crosslinked polymer by virtue of the lysine component of the anhydride. This polymer included PCL and PEG segments as it was prepared using two different diisocyanates: PCL-lysine diisocyanate (LDI-PCL-LDI) and PEG-lysine diisocyanate.

While illustrative embodiments have been illustrated and described, it will be appreciated that various changes can be made therein without departing from the spirit and scope of the invention.

The embodiments of the invention in which an exclusive property or privilege is claimed are defined as follows:

1. A polymer obtainable by the process comprising:
reacting a diisocyanate prepolymer with a diamino acid anhydride to provide a polymer; wherein the diisocyanate prepolymer is prepared by covalently coupling a first diisocyanate compound to a second diisocyanate compound by reaction with a diol or hydroxy acid; and wherein the diamino acid anhydride is prepared by forming an anhydride from a first α-amino acid and a second α-amino acid.

2. The polymer of claim 1, wherein the diol is a poly (ethylene glycol).

3. The polymer of claim 1, wherein the hydroxy acid is selected from the group consisting of 6-hydroxyhexanoic acid, polycaprolactone, lactic acid, poly(lactic acid), glycolic acid, poly(glycolic acid), and poly(lactic acid)-co-poly(glycolic acid).

4. The polymer of claim 1, wherein the first and second diisocyanate compounds are the same.

5. The polymer of claim 1, wherein the first and second diisocyanate compounds are different.

6. The polymer of claim 1, wherein the first and second diisocyanate compounds are independently selected from the group consisting of lysine diisocyanate and $C_1$-$C_5$ alkyl diisocyanates.

7. The polymer of claim 1, wherein the first and second diisocyanate compounds are lysine diisocyanate.

8. The polymer of claim 1, wherein the first amino acid and the second amino acid are the same.

9. The polymer of claim 1, wherein the first amino acid and the second amino acid are different.

10. The polymer of claim 1, wherein the first amino acid and the second amino acid are independently selected from the group consisting of alanine, valine, leucine, isoleucine, proline, methionine, phenylalanine, tryptophan, glycine, serine, threonine, cysteine, tyrosine, asparagines, glutamine, aspartic acid, glutamic acid, lysine, arginine, and histidine.

11. The polymer of claim 1, wherein the first amino acid and the second amino acid are independently selected from the group consisting of lysine, serine, threonine, and tyrosine.

12. The polymer of claim 1, wherein the first amino acid is selected from the group consisting of alanine, valine, leucine, isoleucine, proline, methionine, phenylalanine, tryptophan, glycine, cysteine, asparagines, glutamine, aspartic acid, glutamic acid, arginine, and histidine.

13. The polymer of claim 1, wherein the second amino acid is selected from the group consisting of lysine, serine, threonine, and tyrosine.

14. The polymer of claim 1, wherein the first and second amino acids are lysine.

15. A polymer comprising repeating units having the structure:

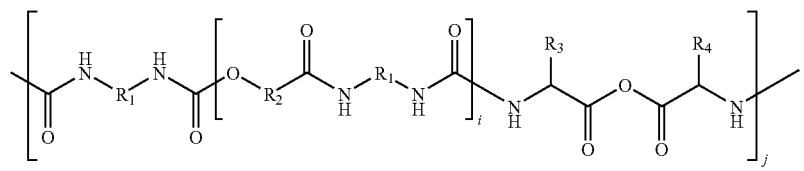

wherein $R_1$ is selected from the group consisting of —(CH(COOCH$_3$)(CH$_2$)$_4$)— and —(CH$_2$)$_k$—, wherein k is an integer from 1 to 5;

$R_2$ is selected from the group consisting of —(CH$_2$CH$_2$O)$_n$—, —(C(=O)(CH$_2$)$_5$O)$_n$—, —(C(=O)CH(CH$_3$)O)$_n$—, —(C(=O)CH$_2$O)$_n$—, and —(C(=O)CH(CH$_3$)O)$_n$—(C(=O)CH$_2$O)$_m$—, wherein n=1-1000 and m=1-1000;

$R_3$ and $R_4$ are independently selected from the group consisting of α-amino acid side chains and their stereoisomers;

i is an integer from 1 to 1000; and j is an integer from 1 to 1000.

16. The polymer of claim 15, wherein at least one of $R_3$ and $R_4$ comprise an amino group, hydroxyl group, or phenol group capable of reacting with an isocyanate to form a covalent bond; and wherein the polymer is crosslinked through the reaction of the polymer repeating units with the group capable of reacting with an isocyanate.

17. The polymer of claim 15, wherein $R_1$ is —(CH(COOCH$_3$)(CH$_2$)$_4$)—.

18. The polymer of claim 15, wherein $R_2$ is —(CH$_2$CH$_2$O)$_n$—, and wherein n is an integer from 1 to 1000.

19. A polymer comprising repeating units having the structure:

wherein $R_1$ is selected from the group consisting of —(CH(COOCH$_3$)(CH$_2$)$_4$)— and —(CH$_2$)$_k$—, wherein k is an integer from 1 to 5;

$R_2$ is selected from the group consisting of —(CH$_2$CH$_2$O)$_n$—, —(C(=O)(CH$_2$)$_5$O)$_n$—, —(C(=O)CH(CH$_3$)O)$_n$—, —(C(=O)CH$_2$O)$_n$—, and —(C(=O)CH(CH$_3$)O)$_n$—(C(=O)CH$_2$O)$_m$—, wherein n is an integer from 1 to 1000 and m is an integer from 1 to 1000;

i is an integer from 1 to 1000; and j is an integer from 1 to 1000.

20. The polymer of claim 19, wherein $R_1$ is —(CH(COOCH$_3$)(CH$_2$)$_4$)—.

21. The polymer of claim 19, wherein $R_2$ is —(CH$_2$CH$_2$O)$_n$—, and wherein n is an integer from 1 to 1000.

22. A biodegradable scaffold for soft tissue engineering comprising a polymer obtainable by the process:

reacting a diisocyanate prepolymer with a diamino acid anhydride to provide a polymer; wherein the diisocyanate prepolymer is prepared by covalently coupling a first diisocyanate compound to a second diisocyanate compound by reaction with a diol or hydroxy acid; and wherein the diamino acid anhydride is prepared by forming an anhydride from a first α-amino acid and a second α-amino acid.

23. The scaffold of claim 22, further comprising a material selected from the group consisting of a gene, a protein, a growth factor, and an antibiotic.

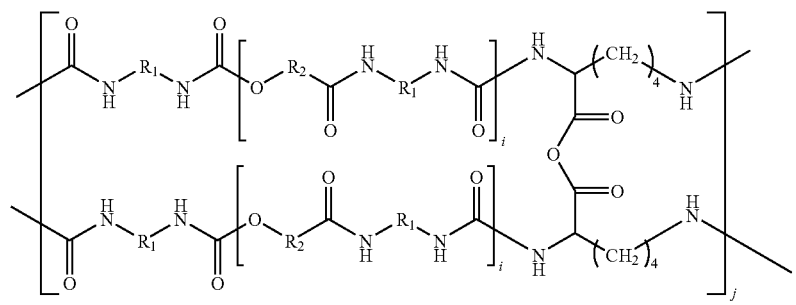

* * * * *